US009845452B2

(12) United States Patent
Kronberg et al.

(10) Patent No.: US 9,845,452 B2
(45) Date of Patent: Dec. 19, 2017

(54) METHODS FOR MODULATING OSTEOCHONDRAL DEVELOPMENT USING BIOELECTRICAL STIMULATION

(71) Applicant: MedRelief Inc., Bethesda, MD (US)

(72) Inventors: James W. Kronberg, Aiken, SC (US); Timothy Ganey, Tampa, FL (US); Stephen L. Gordon, Rockville, MD (US)

(73) Assignee: MEDRELIEF INC., Bethesda, MD (US)

( * ) Notice: Subject to any disclaimer, the term of this patent is extended or adjusted under 35 U.S.C. 154(b) by 0 days.

(21) Appl. No.: 15/463,833

(22) Filed: Mar. 20, 2017

(65) Prior Publication Data

US 2017/0226463 A1    Aug. 10, 2017

Related U.S. Application Data

(60) Continuation of application No. 14/300,024, filed on Jun. 9, 2014, now Pat. No. 9,630,001, which is a
(Continued)

(51) Int. Cl.
  *A61N 1/32*  (2006.01)
  *C12M 1/42*  (2006.01)
(Continued)

(52) U.S. Cl.
  CPC ............. *C12M 35/02* (2013.01); *A61N 1/326* (2013.01); *A61N 1/40* (2013.01); *C12M 21/08* (2013.01)

(58) Field of Classification Search
  None
  See application file for complete search history.

(56) References Cited

U.S. PATENT DOCUMENTS 4,216,548 A    8/1980 Kraus
4,315,503 A    2/1982 Ryaby et al.
(Continued)

FOREIGN PATENT DOCUMENTS

EP    0 561 068 B1    3/1999
JP    2003-516713 A    5/2003
(Continued)

OTHER PUBLICATIONS

Baribault et al., "The G-Protein-Coupled Receptor GPR103 Regulates Bone Formation," *Molecular and Cell Biology* 26(2):709-717, 2006.
(Continued)

*Primary Examiner* — Ankit D Tejani
(74) *Attorney, Agent, or Firm* — Seed IP Law Group LLP

(57) ABSTRACT

Compositions and methods are provided for modulating the growth, development and repair of bone, cartilage or other connective tissue. Devices and stimulus waveforms are provided to differentially modulate the behavior of osteoblasts, chondrocytes and other connective tissue cells to promote proliferation, differentiation, matrix formation or mineralization for in vitro or in vivo applications. Continuous-mode and pulse-burst-mode stimulation of cells with charge-balanced signals may be used. Bone, cartilage and other connective tissue growth is stimulated in part by nitric oxide release through electrical stimulation and may be modulated through co-administration of NO donors and NO synthase inhibitors. Bone, cartilage and other connective tissue growth is stimulated in part by release of BMP-2 and BMP-7 in response to electrical stimulation to promote differentiation of cells. The methods and devices described are useful in promoting repair of bone fractures, cartilage and connective tissue repair as well as for engineering tissue for transplantation.

11 Claims, 8 Drawing Sheets

Related U.S. Application Data division of application No. 12/904,873, filed on Oct. 14, 2010, now Pat. No. 8,785,196, which is a division of application No. 11/444,916, filed on May 22, 2006, now Pat. No. 7,840,272.

(60) Provisional application No. 60/790,128, filed on Apr. 7, 2006, provisional application No. 60/782,462, filed on Mar. 15, 2006, provisional application No. 60/693,490, filed on Jun. 23, 2005, provisional application No. 60/687,430, filed on Jun. 3, 2005.

(51) Int. Cl.
*A61N 1/40* (2006.01)
*C12M 3/00* (2006.01)

(56) References Cited

U.S. PATENT DOCUMENTS

| | | |
|---|---|---|
| 4,729,377 A | 3/1988 | Granek et al. |
| 4,761,216 A | 8/1988 | Cawlfield |
| 5,109,847 A | 5/1992 | Liss et al. |
| 5,218,973 A | 6/1993 | Weaver et al. |
| 5,273,033 A | 12/1993 | Hoffman |
| 5,312,439 A | 5/1994 | Loeb |
| 5,374,283 A | 12/1994 | Flick |
| 5,413,596 A | 5/1995 | Kronberg |
| RE35,129 E | 12/1995 | Pethica et al. |
| 5,487,759 A | 1/1996 | Bastyr et al. |
| 5,520,612 A | 5/1996 | Winder et al. |
| 5,578,060 A | 11/1996 | Pohl et al. |
| 5,578,065 A | 11/1996 | Hattori et al. |
| 5,653,739 A | 8/1997 | Maurer et al. |
| 5,848,966 A | 12/1998 | Gusakov et al. |
| 5,938,690 A | 8/1999 | Law et al. |
| 6,002,695 A | 12/1999 | Alfrey et al. |
| 6,038,477 A | 3/2000 | Kayyali |
| 6,065,154 A | 5/2000 | Hulings et al. |
| 6,130,056 A * | 10/2000 | Correges ............... C12M 41/46 422/504 |
| 6,415,169 B1 | 7/2002 | Kornrumpf et al. |
| 6,535,767 B1 | 3/2003 | Kronberg |
| 6,551,726 B1 | 4/2003 | Burrows |
| 6,564,103 B2 | 5/2003 | Fischer et al. |
| 6,615,080 B1 | 9/2003 | Unsworth et al. |
| 6,675,046 B2 | 1/2004 | Holsheimer |
| 6,684,105 B2 | 1/2004 | Cohen et al. |
| 6,684,106 B2 | 1/2004 | Herbst |
| 6,735,476 B2 | 5/2004 | Mellen |
| 6,751,506 B2 | 6/2004 | Shealy |
| 6,757,564 B2 | 6/2004 | D'Alerta |
| 6,792,315 B2 | 9/2004 | Carter et al. |
| 6,853,863 B2 | 2/2005 | Carter et al. |
| 6,891,107 B2 | 5/2005 | Le Cloirec et al. |
| 6,904,614 B2 | 6/2005 | Yamazaki et al. |
| 6,912,424 B2 | 6/2005 | Bishay et al. |
| 6,915,668 B2 | 7/2005 | Huang et al. |
| 6,919,205 B2 | 7/2005 | Brighton |
| 6,941,173 B2 | 9/2005 | Nachum |
| 6,941,775 B2 | 9/2005 | Sharma |
| 6,944,503 B2 | 9/2005 | Crowe et al. |
| 6,950,700 B2 | 9/2005 | Shealy |
| 6,955,642 B1 | 10/2005 | Simon |
| 6,961,622 B2 | 11/2005 | Gilbert |
| 7,022,506 B2 | 4/2006 | Brighton et al. |
| 7,043,308 B2 | 5/2006 | Cohen |
| 7,089,054 B2 | 8/2006 | Palti |
| 7,120,992 B2 | 10/2006 | He et al. |
| 7,127,296 B2 | 10/2006 | Bradley |
| 7,130,692 B2 | 10/2006 | Brighton et al. |
| 7,149,574 B2 | 12/2006 | Yun et al. |
| 7,167,753 B2 | 1/2007 | Brighton et al. |
| 7,177,696 B1 | 2/2007 | Pandelisev |
| 7,212,854 B2 | 5/2007 | Kovak et a |
| 7,228,179 B2 | 6/2007 | Campen et al. |
| 7,244,150 B1 | 7/2007 | Brase et al. |
| 7,254,447 B2 | 8/2007 | Campos et al. |
| 7,410,497 B2 | 8/2008 | Hastings et al. |
| 2002/0052634 A1 | 5/2002 | March |
| 2002/0115208 A1 | 8/2002 | Mitchell et al. |
| 2002/0120309 A1 | 8/2002 | Richmond et al. |
| 2004/0005297 A1 | 1/2004 | Connelly et al. |
| 2004/0140053 A1 | 7/2004 | Srivastava et al. |
| 2004/0210282 A1 | 10/2004 | Flock et al. |
| 2004/0267333 A1 | 12/2004 | Kronberg |
| 2005/0014129 A1* | 1/2005 | Cliffel ............... G01N 33/5005 435/4 |
| 2005/0049640 A1 | 3/2005 | Gurtner et al. |
| 2005/0070971 A1 | 3/2005 | Fowler et al. |
| 2005/0084962 A1 | 4/2005 | Simon |
| 2005/0119712 A1 | 6/2005 | Shafer |
| 2007/0299472 A1 | 12/2007 | Brighton |

FOREIGN PATENT DOCUMENTS

| | | |
|---|---|---|
| TW | 283087 B | 8/1996 |
| WO | 03/015866 A2 | 2/2003 |
| WO | 2007/131809 A1 | 11/2007 |

OTHER PUBLICATIONS

Bowler et al., "G-Protein Coupled Receptors in Bone," *Frontiers in Bioscience* 3:d769-780, 1998.

Bodamyali et al., "Pulsed Electromagnetic Fields Simultaneously Induce Osteogenesis and Upregulate Transcription of Bone Morphogenetic Proteins 2 and 4 in Rat Osteoblasts in Vitro," *Biochemical and Biophysical Research Communications* 250(2):458-461, 1998.

Ciombor et al., "The Role of Electrical Stimulation in Bone Repair," *Foot and Ankle Clinics* 10(4): 579-593, 2005.

European Search Report for European Application No. 06771526.8-2305/1888162, dated Aug. 10, 2009, 6 pages.

First Examination Report for Indian Application No. 4808/KOLNP/2007, dated Feb. 23, 2011, 5 pages.

Ganey et al., "Effect of PEMF Signal: Mineralization and Morphology in a Primary Osteoblast Culture," U.S. Appl. No. 60/693,430, filed Jun. 23, 2005, 17 pages.

Henrotin et al., "The role of reactive oxygen species in homeostasis and degradation of cartilage," *OsteoArthritis and Cartilage* 11:747-755, 2003.

International Search Report for International Application No. PCT/US06/20819, dated Aug. 3, 2007, 1 page.

International Search Report for International Application No. PCT/US07/13766, dated Aug. 26, 2008.

Kronberg et al., "Methods of Evaluating and Stimulating Cell Culture Using PEMF Signal Application," U.S. Appl. No. 60/687,430, filed Jun. 3, 2005, 12 pages.

Kronberg et al., "Methods for Modulation Bone Development," U.S. Appl. No. 60/790,128, filed Apr. 7, 2006, 20 pages.

Kronberg et al., Effect of PEMF Signal Configuration on Mineralization and Morphology in a Primary Osteoblast Culture, U.S. Appl. No. 60/782,462, filed Mar. 15, 2006, 2 pages.

Seeherman et al., "Delivery of bone morphogenetic proteins for orthopedic tissue regeneration, *Cytokine Growth Factor Reviews*," 16(3):329-345, 2005.

Struder et al., "Nitric oxide inhibition of IGF-1 stimulated proteoglycan synthesis: role of cGMP," *Journal of Orthopaedic Research* 21:914-921, 2003.

Office Action with English translation for Japanese Patent Application No. 2008-514764, dated Dec. 6, 2011, 9 pages.

Office Action for Mexican Patent Application No. MX/a/2007/015302, dated Jun. 20, 2011, 6 pages.

Takigawa et al., "Role of CTGF/HCS24/Ecogenin in Skeletal Growth Control," *Journal of Cellular Physiology* 194:256-266, 2003.

United Arab Emirates Search Report, dated Aug. 22, 2014, for corresponding UAE Application No. UAE/P/1117/2007, 13 pages.

Van't Hof et al., "Nitric oxide and bone," *Immunology* 103:255-261, 2001.

(56) References Cited

OTHER PUBLICATIONS

Written Opinion of the International Searching Authority for International Application No. PCT/US06/20819, dated Aug. 3, 2007, 4 pages.
Written Opinion of the International Searching Authority for International Application No. PCT/US07/13766, dated Aug. 26, 2008, 3 pages.

* cited by examiner

METHODS FOR MODULATING OSTEOCHONDRAL DEVELOPMENT USING BIOELECTRICAL STIMULATION

BACKGROUND

Diseases and injuries associated with bone and cartilage have a significant impact on the population. Approximately five million bone fractures occur annually in the United States alone. About 10% of these have delayed healing and of these, 150,000 to 200,000 nonunion fractures occur accompanied by loss of productivity and independence. In the case of cartilage, severe and chronic forms of knee joint cartilage damage can lead to greater deterioration of the joint cartilage and may eventually lead to a total knee joint replacement. Approximately 200,000 total knee replacement operations are performed annually and the artificial joint generally lasts only 10 to 15 years leading to similar losses in productivity and independence.

Furthermore, the incidence of bone fractures is also expected to remain high in view of the incidence of osteoporosis as a major public health threat for an estimated 44 million Americans. In the U.S. today, 10 million individuals are estimated to already have the disease and almost 34 million more are estimated to have low bone mass, placing them at increased risk for osteoporosis. One in two women and one in four men over age 50 will have an osteoporosis-related fracture in their remaining life. Osteoporosis is responsible for more than 1.5 million fractures annually, including: 300,000 hip fractures; 700,000 vertebral fractures; 250,000 wrist fractures; and 300,000 fractures at other sites. The estimated national direct expenditures (hospitals and nursing homes) for osteoporotic hip fractures were $18 Billion in 2002 (National Osteoporosis Foundation Annual Report, 2002).

Several treatments are currently available to treat recalcitrant fractures such as internal and external fixation, bone grafts or graft substitutes including demineralized bone matrix, platelet extracts and bone matrix protein, and biophysical stimulation such as mechanical strain applied through external fixators or ultrasound and electromagnetic fields.

Similarly, typical treatment for cartilage injury, depending on lesion and symptom severity, are rest and other conservative treatments, minor arthroscopic surgery to clean up and smooth the surface of the damaged cartilage area, and other surgical procedures such as microfracture, drilling, and abrasion. All of these may provide symptomatic relief, but the benefit is usually only temporary, especially if the person's pre-injury activity level is maintained.

Bone and other tissues such as cartilage respond to electrical signals in a physiologically useful manner. Bioelectrical stimulation devices applied to non-unions and delayed unions were initiated in the 1960s and is now applied to bone and cartilage (Ciombor and Aaron, Foot Ankle Clin. 2005, (4):579-93). Currently, a market and general acceptance of their role in clinical practice has been established. Less well-known outcomes attributed to bioelectrical stimulation are positive bone density changes (Tabrah, 1990), and prevention of osteoporosis (Chang, 2003). A recent report offered adjunctive evidence that stimulation with pulsed electromagnetic field (PEMF) significantly accelerates bone formed during distraction osteogenesis (Fredericks, 2003).

At present, clinical use of electrotherapy for bone repair consists of electrodes implanted directly into the repair site or noninvasive capacitive or inductive coupling. Direct current (DC) is applied via one electrode (cathode) placed in the tissue target at the site of bone repair and the anode placed in soft tissues. DC currents of 5-100 µA are sufficient to stimulate osteogenesis. The capacitative coupling technique uses external skin electrodes placed on opposite sides of the fracture site. Sinusoidal waves of 20-200 Hz are typically employed to induce 1-100 mV/cm electric fields in the repair site.

The inductive coupling (PEMF) technique induces a time-varying electric field at the repair site by applying a time-varying magnetic field via one or two electrical coils. The induced electric field acts as a triggering mechanism which modulates the normal process of molecular regulation of bone repair mediated by many growth factors. Bassett et al., were the first to report a PEMF signal could accelerate bone repair by 150% in a canine. Experimental models of bone repair show enhanced cell proliferation, calcification, and increased mechanical strength with DC currents. Such approaches also hold potential for cartilage injuries.

Wounded tissue has an electrical potential relative to normal tissue. Electrical signals measured at wound sites, termed the "injury potential" or "current of injury", are DC (direct current) only, changing slowly with time. Bone fracture repair and nerve re-growth potentials are typically faster than usual in the vicinity of a negative electrode but slower near a positive one, where in some cases tissue atrophy or necrosis may occur. For this reason, most recent research has focused on higher-frequency, more complex signals often with no net DC component.

Unfortunately, most electrotherapeutic devices now available rely on direct implantation of electrodes or entire electronic packages, or on inductive coupling through the skin using coils which generate time-varying magnetic fields, thereby inducing weak eddy currents within body tissues which inefficiently provides the signal to tissues and thus in addition to bulky coils requires relatively large signal generators and battery packs. The need for surgery and biocompatible materials in the one case, and excessive circuit complexity and input power in the other, has kept the price of most such apparatus relatively high, and has also restricted the application of such devices to highly trained personnel. There remains a need, therefore, for a versatile, cost-effective apparatus that can be used to provide bioelectric stimulation to differentially modulate the growth of osteochondral tissue to promote proper development and healing.

SUMMARY OF THE INVENTION

According to its major aspects and broadly stated, the present invention provides a method for modulating the growth or repair of, for example bone tissue or cartilage, by administering an electrical signal to developing or damaged bone or cartilage tissue.

The present invention overcomes the shortcomings of prior art devices and methods by enabling the delivery of bioelectrical signals optimized to correspond to selected features of natural body signals resulting in accelerated and more permanent healing. The signals described herein conform to selected features of natural signals and consequently tissues subjected to electrostimulation according to the present invention undergo minimal physiological stress. In addition, the present invention is non-invasive and cost-effective making it desirable for multiple applications for personal and individual use. Furthermore, the present methods provide electrical stimulation where the electrical signals closely mimic selected characteristics of natural body signals. The stimulated tissue is therefore subjected to minimal stress and growth and repair is greatly facilitated.

In contrast to conventional TENS-type devices, which are aimed at blocking pain impulses in the nervous system, the apparatus used with the present methods operates at a stimulus level which is below the normal human threshold level of pain sensation and as such, most users do not experience any sensation during treatment to repair or promote growth of bone.

The technology described herein uses a class of waveforms, some of which are novel and other which are known to have positive biological effects on tissues when applied through inductive coils, but have not been demonstrated to have positive biological effects through electrodes until now.

Although no commercial bioelectrical devices are currently approved for osteoporosis therapy, the present invention provides a promising candidate. As demonstrated herein, unique pulsed electromagnetic field (PEMF) wave patterns may be advantageously applied at both a macroscopic level (i.e. common bone fractures) as well as at microscopic levels (i.e. osteoblast development). Certain embodiments of the invention maximize the utility and application of desired PEMF waveforms: for example, the spine, hip and/or wrist are the most common sites of osteoporotic fracture, for such types of fractures the inventors provide simple, self-adhesive, skin contact electrode pads as electrotherapeutic delivery vehicles. The use of such electrode pads results in the improvement of bone mass at such key anatomical sites. At a microscopic level, the present inventors have identified specific PEMF waveforms and frequencies that optimize osteoblast development. As described in greater detail in the Examples (see Example 1) the inventors demonstrate that PEMF signals enhance osteoblast mineralization and matrix production, and that the signal confers structural features as well. The inventors also show that other PEMF signals enhanced cell proliferation and accompanying increases in bone morphogenetic proteins (BMPs). While both pulse-burst and continuous electrical signals may be used in the present invention, the administration of continuous rather than pulse-burst signals provided the more pronounced effects on proliferation and mineralization.

The electrical signals of the present invention may be used to promote the repair and growth of structural tissues such as bone and cartilage. However, such systems and methods need not be confined to use with intact organisms, since isolated cells or tissue cultures can also be affected by electrotherapeutic waveforms (appropriate electrical stimuli have been observed to modify the rates of cell metabolism, secretion, and replication). Electrical signals are generally applicable to other connective tissues such as skin, ligaments, tendons, and the like. The electrical signals described herein may be used to stimulate other tissues to increase repair of the tissues and promote growth of tissues for transplantation purposes. Isolated skin cells, for example, might be treated with the devices and waveforms of the present invention in an appropriate growth medium to increase cell proliferation and differentiation in the preparation of tissue-cultured, autogenous skin-graft material. In a like manner, these bioelectric signals can be applied directly to injured or diseased skin tissue to enhance healing.

Exogenous delivery of bioelectrical signals and progenitor cells such as bone marrow stromal cells-BMSCs to a fracture can lead to enhanced healing and repair of recalcitrant fractures. Both of these factors (bioelectricity and cell recruitment) are, in fact, parts of the natural healing process. For these applications, electrical stimulation using the waveforms described herein can be applied immediately after injury with an electrotherapy system. The electrotherapy system may be lightweight, compact and portable. Both electrical stimulation and universal cell-based therapy can be applied within a few days after injury. Autologous cells may be added at time further after injury. The present invention also provides methods to induce bone repair or development that regenerates natural tissues rather than scar tissue.

Accordingly, it is an object of the present invention to provide methods for modulating the proliferation and differentiation of bone tissue for facilitation of bone repair and development by administering novel electrical signals to bone tissue.

It is another object of the present invention to provide novel culture systems comprising the use of PEMF for bone tissue engineering.

It is another object of the present invention to provide novel culture systems of progenitor cells in combination with electrical stimulation.

It is another object of the present invention to provide kits for the growth of autologous and allogeneic tissues for transplantation into a host in need thereof.

It is another object of the present invention to provide methods for electrically stimulating uncommitted progenitor cells in vitro or in vivo to induce proliferation or differentiation.

It is another object of the present invention to provide methods for modulating the growth of cartilage, bone or other connective tissue.

It is another object of the present invention to provide methods for modulating the expression and release of bone morphogenic proteins.

These and other objects, features, and advantages of the present invention will become apparent after review of the following detailed description of the disclosed embodiments and the appended claims.

DETAILED DESCRIPTION OF THE INVENTION

Figure 1:
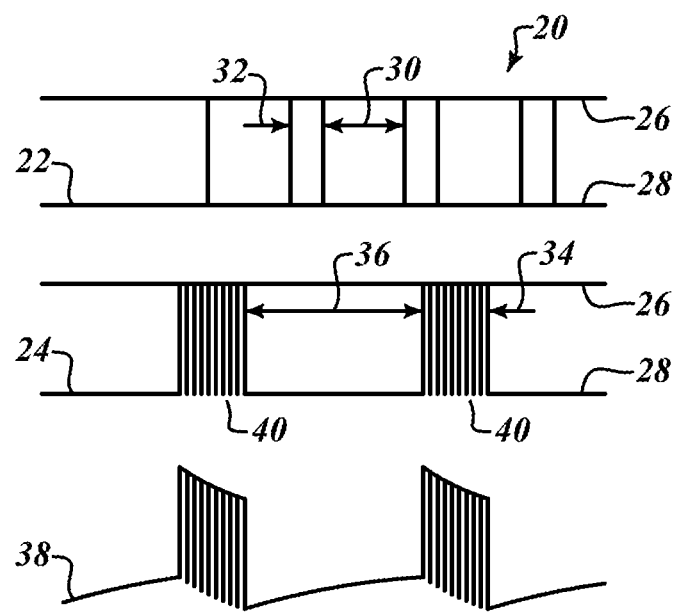
FIG. 1 is a schematic view of a waveform used in stimulating bone fracture healing.

The following description includes the best presently contemplated mode of carrying out the invention. This description is made for the purpose of illustrating the general principles of the inventions and should not be taken in a limiting sense. The text of the references mentioned herein are hereby incorporated in their entireties by reference, including U.S. Provisional Application Ser. Nos. 60/687,430, 60/693,490, 60/782,462 and 60/790,128.

It should be understood that the present in vitro applications of the invention described herein may also be extrapolated for in vivo applications, therapies and the like. One of ordinary skill will appreciate that technology developed using reduced preparations and in vitro models may ultimately be used for in vivo applications. Effective values and ranges for electrical stimulation in vivo may be extrapolated from dose-response curves derived from in vitro or animal model test systems.

The present invention enables the delivery of bioelectrical signals optimized to correspond to selected characteristics of natural body signals resulting in accelerated and more permanent healing. The signals described herein uniquely conform to selected features of natural signals and consequently tissues subjected to electrostimulation according to the present invention undergo minimal physiological stress. In addition, the present invention is non-invasive and cost-effective making it desirable for multiple applications for personal and individual use.

Bone Remodeling

Bone is one of the most rigid tissues of the human body. As the main component of the human skeleton, it not only supports muscular structures but protects vital organs in the cranial and thoracic cavities. Bone is composed of intercellular calcified material (the bone extracellular matrix) and different cell types: osteoblasts, osteocytes and osteoclasts. The extracellular matrix is composed of organic and inorganic components. The organic component includes cells, collagens, proteoglycans, hyaluronan and other proteins, phospholipids and growth factors. The rigidity of bone comes from the mineralized inorganic component which is predominantly calcium and phosphorus crystallized in the form of hydroxyapatite $Ca_{10}(PO_4)_6(OH)_2$. The combination of collagen and hydroxyapatite confers the hardness and stiffness characteristics of bone.

Osteoblasts are derived from progenitor cells of mesenchymal origin and are localized at the surfaces next to emerging bone matrix and arranged side-by-side. The primary function of osteoblasts is the elaboration and development of bone matrix and to play a role in matrix mineralization. Osteoblasts are called osteocytes when embedded in the lacunae of the bone matrix and adopt a slightly different morphology and retain contact with other osteocytes. Osteoclasts are larger multinucleate cells containing receptors for calcitonin and integrin and other specialized structural features. The primary function of osteoclasts is to resorb both inorganic and organic components of calcified bone matrix.

Bone remodeling is the fundamental and highly integrated process of resorption and formation of bone tissue that results in precisely balanced skeletal mass with renewal of the mineralized matrix. This renewable process is achieved without compromising the overall anatomical architecture of bones. This continuous process of internal turnover ensures that bone maintains a capacity for true regeneration and maintenance of bone integrity by continuous repairing of microfractures and alterations in response to stress. The architecture and composition of the adult skeleton is in perpetually dynamic equilibrium. Remodeling also provides a means for release of calcium in response to homeostatic demands. Conditions that influence bone remodeling include mechanical stimuli such as immobilization or weightlessness, electric current or electromagnetic fields such as capacitively coupled electric field or pulsed electromagnetic field, hormonal changes or in response to certain inflammatory diseases.

Bone remodeling occurs through orchestrated cycles of activity that include activation, resorption, reversal, formation, and quiescence steps. Activation is characterized by the existence of a thin layer of lining cells. Then circulating mononuclear cells of hematopoetic lineage begin to migrate into the activation site and fuse together to form osteoclasts. Activation is followed by resorption where active osteoclasts excavate a bony surface. This step typically lasts about 2-4 weeks. Reversal occurs following resorption and continues for a period of 9 days during this time inactive pre-osteoblasts are present in the resorption depressions. The next step is formation and takes about 3-4 months. During this stage active osteoblasts refill the excavation site. The last phase of bone remodeling is quiescence where no remodeling activity occurs until the beginning of the next remodeling cycle. Ideally the quantity of bone fill must equal the quantity resorbed with no loss of bone mass.

Waveforms

The present invention provides electrical signals and waveforms that enable specific actions on biological tissues. Such waveforms are effective for both in vivo and in vitro applications. Osteochondral tissues are shown herein to respond differently to markedly different frequencies and waveforms.

Of particular interest are signals comprising alternating rectangular or quasirectangular pulses having opposite polarities and unequal lengths, thereby forming rectangular, asymmetric pulse trains. Pulses of specific lengths have been theorized to activate specific cell biochemical mechanisms, especially the binding of calcium or other small, mobile, charged species to receptors on the cell membrane, or their (usually slower) unbinding. The portions of such a train having opposite polarities may balance to yield substantially a net zero charge, and the train may be either continuous or divided into pulse bursts separated by intervals of substantially zero signal. Stimuli administered in pulse-burst mode have similar actions to those administered as continuous trains, but their actions may differ in detail due to the ability (theoretically) of charged species to unbind from receptors during the zero-signal periods, and required administration schedules may also differ.

FIG. 1 shows a schematic view of a base waveform 20 effective for stimulating bone and cartilage tissue, where a line 22 represents the waveform in continuous mode, and line 24 represents the same waveform on a longer time scale in pulse-burst mode, levels 26 and 28 represent two different characteristic values of voltage or current, and intervals 30, 32, 34 and 36 represent the timing between specific transitions. Levels 26 and 28 are usually selected so that, when averaged over a full cycle of the waveform, there is no net direct-current (D.C.) component although levels 26 and 28 may be selected to result in a net positive or net negative D.C. component if desired. In real-world applications, waveform such as 20 is typically modified in that all voltages or currents decay exponentially toward some intermediate level between levels 26 and 28, with a decay time constant preferably longer than interval 34. The result is represented by a line 38. The waveforms described herein generally have two signal components: a longer component shown as interval 30 and a shorter component shown as interval 32 relative to each other.

Variation in the short and long signal component lengths confers specific effects of a stimulated tissue. Pulse lengths of interest in this invention may be defined as follows, in order of increasing length:

Length $\alpha$: between 5 and 75 μsec in duration, preferably between 10 and 50 μsec in duration, more preferably between 20 and 35 μsec in duration and most preferably about 28 μsec in duration.

Length $\beta$: between 20 and 100 μsec in duration, preferably between 40 and 80 μsec in duration, more preferably between 50 and 70 μsec in duration and most preferably about 60 μsec in duration.

Length $\gamma$: between 100 and 1000 μsec in duration, preferably between 150 and 800 μsec in duration, more preferably between 180 and 500 μsec in duration and most preferably about 200 μsec in duration.

Length $\delta$: in excess of 1 millisecond in duration, preferably between 5 and 100 msec in duration, more preferably between 10 and 20 msec in duration and most preferably about 13 msec in duration.

Figure 2A:
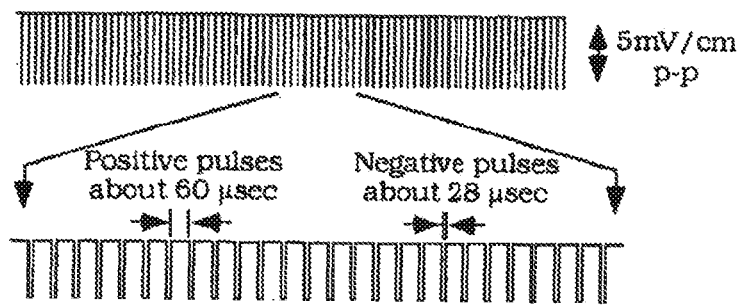
FIG. 2A provides an illustration showing an effective electrical signal waveform in pulse mode based on an inductive, coil waveform and adapted for skin application for promoting mineralization of bone.

In a first embodiment the electrical signal has a shorter component of length $\alpha$ and a longer component of length $\beta$: thus having, with the most preferable pulse lengths of each type (28 μsec and 60 μsec respectively), a frequency of about 11.4 KHz. Signals comprised of pulses alternately of length $\alpha$ and length $\beta$ are referred to herein as "type A" signals and their waveforms as "type A" waveforms. An example a "type-A signal administered as a continuous pulse train is shown in FIG. 2A. Signals such as this are useful for promoting the proliferation of a tissue sample or culture for a variety of biological or therapeutic applications.

Figure 2B:
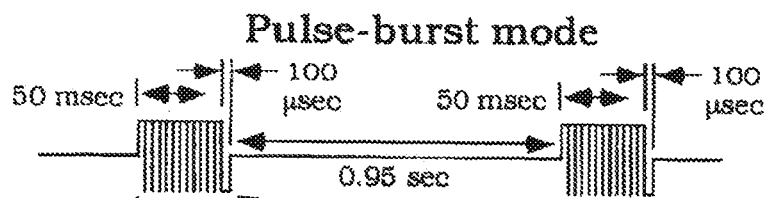
FIG. 2B provides an illustration showing an effective electrical signal waveform in continuous mode for promoting mineralization of bone.

In pulse-burst mode, "type A" waveforms would be turned on in bursts of about 0.5 to 500 msec, preferably about 50 msec, with bursts repeated at 0.1-10 Hz or preferably about 1 Hz. An example of this type of waveform is shown in FIG. 2B.

Figure 3A:
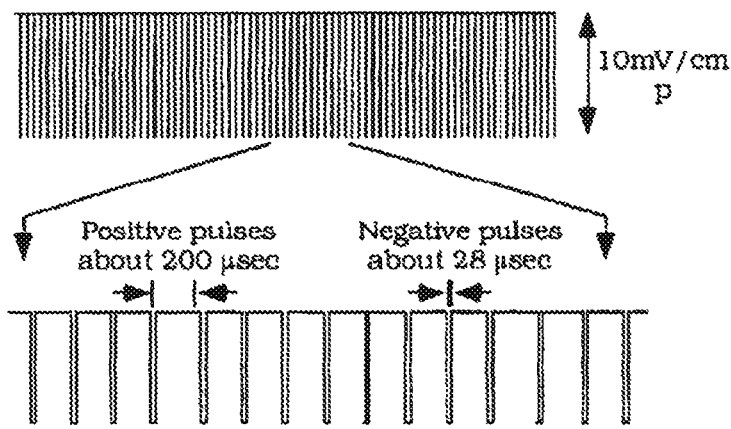
FIG. 3A provides an illustration showing an effective electrical signal waveform in pulse mode for promoting proliferation of bone cells.

In a second embodiment the electrical signal has a shorter component of length $\alpha$ but a longer component of length $\gamma$: thus having, with the most preferable pulse lengths of each type (28 μsec and 200 μsec respectively), a frequency of about 4.4 KHz. Signals comprised of pulses alternately of length $\alpha$ and length $\gamma$ are referred to herein as "type B" signals and their waveforms as "type B" waveforms. Such waveforms were previously described in U.S. patent application Ser. No. 10/875,801 (publication no. 2004/0267333). An example of a "type-B" signal administered as a continuous pulse train is shown in FIG. 3A. Signals such as this are useful in pain relief and in promoting bone healing, and also stimulate the development of cancellous-bone-like structures in osteoblast cultures in vitro, with applications to the field of surgical bone repair and grafting materials.

Figure 3B:
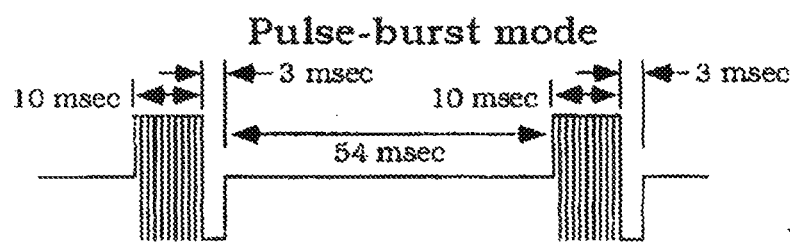
FIG. 3B provides an illustration showing an effective electrical signal waveform in continuous mode for promoting proliferation of bone cells.

In pulse-burst mode, "type B" waveforms are turned on in bursts of about 1 to 50 msec, preferably about 5 msec, with bursts repeated at 5-100 Hz or preferably about 15 Hz. An example of this type of waveform is shown in FIG. 3B. This waveform is similar in shape and amplitude to effective currents delivered by typical inductive (coil) electromagnetic devices that are commonly used in non-union bone stimulation products e.g. EBI MEDICA, INC.® (Parsippany, N.J.) and ORTHOFIX, INC.® (McKinney, Tex.).

In a third embodiment the electrical signal has a shorter component of length $\beta$ but a longer component of length $\gamma$: thus having, with the most preferable pulse lengths of each type (60 μsec and 200 μsec respectively) a frequency of about 3.8 KHz. Signals comprised of pulses alternately of length $\beta$ and length $\gamma$ are referred to herein as "type C" signals and their waveforms as "type C" waveforms. Signals such as this are useful in promoting bone regeneration, maturation and calcification.

In pulse-burst mode, "type C" waveforms are turned on in bursts of about 1 to 50 msec, preferably about 5 msec, with bursts repeated at 5-100 Hz or preferably about 15 Hz, much the same as "type B." This waveform is similar in shape and amplitude to effective currents delivered by other typical inductive (coil) electromagnetic devices commonly used in non-union bone stimulation products, e.g. the ORTHOFIX, INC.® (McKinney, Tex.) PhysioStim Lite® which is designed to promote healing of spinal fusions.

Figure 3B:
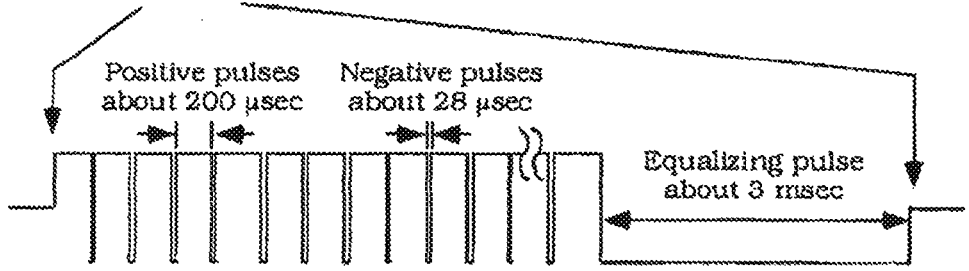

In a fourth embodiment the electrical signal has a shorter component of length $\gamma$ and a longer component of length $\delta$: thus having, with the most preferable pulse lengths of each type (200 μsec and 13 msec respectively) a frequency of about 75 Hz. Signals comprised of pulses alternately of length $\gamma$ and length $\delta$ are referred to herein as "type D" signals and their waveforms as "type D" waveforms. Signals such as this are useful especially in promoting cartilage healing and bone calcification, and in treating or reversing osteoporosis and osteoarthritis. While broadly similar to that delivered through electrodes by the BIONICARE MEDICAL TECHNOLOGIES INC.® BIO-1000™, as shown in FIG. 3 of U.S. Pat. No. 5,273,033 which is here incorporated by reference, the "type D" signal differs substantially in wave shape (it is rectangular rather than exponential) and in the fact that it is preferably charge-balanced.

In pulse-burst mode, "type D" waveforms are turned on in bursts of at least 100 msec, preferably about 1 second, with bursts repeated at intervals of one second or more.

The signal intensity may also vary; indeed, more powerful signals often give no more benefit than weaker ones, and sometimes less. For a typical signal (such as the signal of FIG. 1), a peak effectiveness typically falls somewhere between one and ten microamperes per square centimeter ($\mu A/cm^2$), and a crossover point at about a hundred times this value. Beyond this point, the signal may slow healing or may itself cause further injury.

Of particular relevance to the present methods are electrical signals or waveforms, that run in continuous mode instead of burst mode. (For example FIG. 2A or 3A). Continuously run signals have effects similar to those of pulse-burst signals, but may require different delivery schedules to achieve similar results.

For the waveforms used with the methods of the present invention, typical applied average current densities are between 0.1 and 1000 microamperes per square centimeter, preferably between 0.3 and 300 microamperes per square centimeter, more preferably between 1 and 100 microamperes per square centimeter, and most preferably about 10 microamperes per square centimeter, resulting in voltage gradients ranging between 0.01 and 1000, 0.03 and 300, 0.1 and 100, and 1 and 10 microamperes per centimeter, respectively, in typical body tissues. The individual nearly-square wave signal is asynchronous with a long positive segment and a short negative segment or vice versa. The positive and negative portions balance to yield a zero net charge or optionally may be charge imbalanced with an equalizing pulse at the end of the pulse to provide zero net charge balance over the waveform as a whole. These waveforms delivered by skin electrodes use continuous rectangular or approximately rectangular rather than sinusoidal or strongly exponentially decaying waveforms. Other waveforms useful in the methods of the present invention are disclosed in published U.S. patent application Ser. No. 10/875,801 (publication no. 2004/0267333) incorporated herein by reference in its entirety.

The electrical signals described above may be administered to cells, biological tissues or individuals in need of treatment for intermittent treatment intervals or continuously throughout the day. A treatment interval is defined herein as a time interval that a waveform is administered in pulse or continuous mode. Treatment intervals may be about 10 minutes to about 4 hours in duration, about 30 minutes to about 2.5 hours in duration or about 1 hour in duration. Treatment intervals may occur between about 1 and 100 times per day. The duration and frequency of treatment intervals may be adjusted for each case to obtain an effective amount of electrical stimulation to promote cell proliferation, cell differentiation, bone growth, development or repair. The parameters are adjusted to determine the most effective treatment parameters.

Signals do not necessarily require long hours of duration in the treatment interval although 24 hours administration may be used if desired. Typically, 30 minutes (repeated several times a day) is required for biological effectiveness. In vitro cell proliferation may be measured by standard means such as cell counts, increases in nucleic acid or protein synthesis. Upregulation or down regulation of matrix proteins (collagen types I, III, and IV) as well as growth factors and cytokines (such as TGF-B, VEGF, SLPI, FN, MMPs) may also be measured (mRNA and protein synthesis). In vivo effects may be determined by rate of healing of an injury or measuring bone mass density. Other diagnostic methods for proliferation, differentiation or mineralization of bone tissue will be readily apparent to one of ordinary skill.

In one embodiment, proliferation-promoting and differentiation-promoting signals are used sequentially. This combination of waveforms is used to increase the cell number and then promote differentiation of the cells. As an example, the sequential use of proliferation and differentiation signals may be used to promote proliferation of osteoblasts and then differentiation of the osteoblasts into mineral producing osteocytes that promote mineralization of bone or vice versa. For example, a treatment paradigm may be used where a proliferation-promoting A-type signal is administered first to a cell population in vitro or ex vivo for hours, days or weeks and then the proliferation promoting signal is replaced with a mineralization-promoting B-type signal for hours, days or weeks until bone mineralization has been effected. The tissue produced may then be transplanted for patient benefit. Both signals may also be applied simultaneously to promote both proliferation, differentiation and mineralization simultaneously.

The electric signals may be delivered by skin electrodes, or electrochemical connection. Skin electrodes are available commercially in sizes such as 1½×12, 2×3½, and 2×2 inches that may be useful for application to the spine, hips, and arm, respectively. These reusable electrodes are advantageous because they do not contain latex and have not shown significant skin irritation. The reusable electrodes can be used multiple times; also reducing costs to the patient. Such electrodes may include electrodes #214 (⅕"×13"), #220 (2"×2") and #230 (2"×⅗") (KOALATY PRODUCTS®, Tampa, Fla.) or electrodes #T2020 (2"×2") and #T2030 (2"×3.5") (VERMED, INC®, Bellows Falls, Vt.).

There are multiple advantages of using skin electrodes instead of electromagnetic coils. Firstly, skin electrodes are more efficient. With electrodes, only the signal which will actually be sent into the body must be generated. With a coil, because of poor electromagnetic coupling with the tissues, the signal put in must be many, many times stronger than that desired in the tissues. This makes the required generating circuitry for electrodes potentially much simpler than for coils, while requiring much less power to operate. Secondly, skin electrodes are more user friendly. Skin electrodes have at most a few percent of the weight and bulk of coils needed to deliver equivalent signal levels. Similarly, because of better coupling efficiency the signal generators to drive electrodes can be made much smaller and lighter than those for coils. After a short time, a wearer hardly notices they are there. Thirdly, skin electrodes are more economical. Unlike coils, which cost hundreds to thousands of dollars each, electrodes are "throw-away" items typically costing less than a dollar. Also, because of greater efficiency and simplicity, the signal generators and batteries to drive them can be small and inexpensive to manufacture compared with those for coils. Fourthly, skin electrodes permit simpler battery construction and longer battery life facilitating the ease and patient compliance of using the device. Lastly, skin electrodes are more versatile than electromagnetic coils. Coils must be built to match the geometric characteristics of body parts to which they will be applied, and each must be large enough to surround or enclose the part to be treated. This means to "cover" the body there must be many, many different coil sizes and shapes, some of them quite large. With electrodes, on the other hand, current distribution is determined by electrode placement only and readily predictable throughout the volume between, so the body may be "covered" with just a few electrode types plus a list of well-chosen placements.

Stimulation Systems

Also contemplated by the present invention are biological systems that include cells and stimulators for delivering electrical signals to cells. Such cells may include, but are not limited to, precursor cells such as stem cells, uncommitted progenitors, committed progenitor cells, multipotent progenitors, pluripotent progenitors or cells at other stages of differentiation. Such cells may be embryonic, fetal, or adult cells and may be harvested or isolated from autologous or allogeneic sources. In one embodiment proliferative cells are used although non-proliferative cells may also be used in the methods described herein. Such cells may be combined in vitro, for example in tissue culture, or in vivo for tissue engineering or tissue repair applications. Transplanted stem cells may be selectively attracted to sites of injury or disease and then electrically stimulated to provide enhanced heating.

Stimulating cell cultures in accordance with the method and purpose of the present invention also requires a practical means of delivering uniform waveforms simultaneously to many culture wells without disturbing the incubation process or causing contamination. Devices are provided herein for electrically stimulating cultures during incubation that preferably contain six tissue culture wells connected as a multi-well system using specially designed capacitively coupled anodized electrode systems for signal administration. By using a ribbon cable attachment, leaks at the seal of the incubator are minimized maintaining the controlled $CO_2$ environment for the cultures. A typical setup is shown, in partly schematic form, in FIG. 4.

Figure 4:
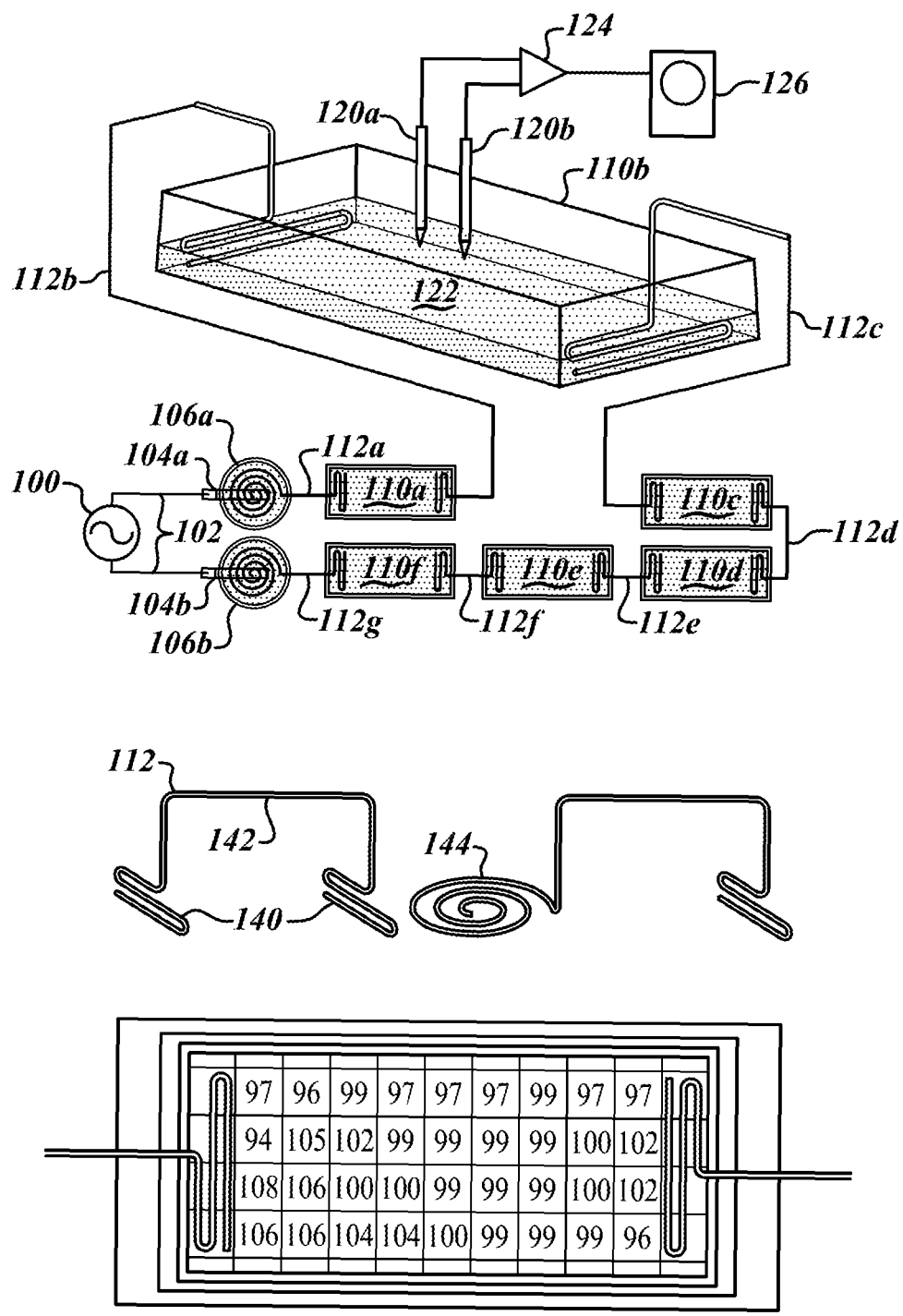
FIG. 4 provides an illustration showing an experimental lab chamber for delivering current.

In the setup shown for example in FIG. 4, six tissue culture wells 110a through 110f are interconnected and each well includes electrodes 140 at the chamber ends formed by two 15-mm and one 7.5-mm straight segments of wire, joined by hairpin bends and connected by a right-angle bend to the central part 142 of the bridge 112. Seven such bridges are shown in FIG. 4. The electrodes 140 are sized to fit the end walls of a Lab-Tek II slide chamber, which measures 18 by 48 millimeters internally with a typical 3-mm fill depth. The capacitance of such an electrode is about 0.56 microfarad. Bridges 112a and 112g differ in having end-well spirals 144 each containing about 15 cm of wire. The resulting capacitance between the bridge wire 112a or 112g and the corresponding silver electrode 104, is about 2.3 microfarads.

Bridges 112a, 112b and so forth, formed of solid, relatively inert metal, connect chambers 110a, 110b and so forth electrically in series between end wells 106a and 106b. While six chambers 110a through 110f, and seven bridges 112a through 112g, are shown here, any other convenient numbers "n" of chambers and "n+1" of bridges could be used. In addition, a plurality of such series-connected groups each comprised of "n" chambers, "n+1" bridges and two end wells could be used with a single signal source 100, using a signal distribution means such as a resistor network to divide the signal energy among the groups, as is well known in the art of electronic signaling.

The total electrical impedance of the setup shown, with twelve chamber electrode ends, two end-well spiral electrode 106 and six chambers as described, is chiefly capacitive at 0.045 microfarad plus a resistive component of about 10,000 ohms. A series resistor (not shown) connected between signal source 100 and end well 106a can both regulate the applied current to a desired level and also "swamp out" the capacitive part of the series reactance. For example, with a 1-Megohm resistor the frequency response is uniform within +/−3 dB from 5 Hz to 3 Mhz.

If desired, the signal energy distribution in a chamber may be measured with probes as shown in the magnified chamber 110b. Probes 120, made of any reasonably inert metal but preferably of 99.9% pure silver as electrodes 104a and 104b, insulated except at their tips, and with these tips set a known and fixed distance apart, are immersed in medium 122 and moved into a succession of positions, preferably marking a rectangular grid. The differential voltage at each position is read by a differential amplifier 124, such as an Analog Devices AD522, and sent to an oscilloscope or other device, generally indicated by 126, for display or recording. The results are conveniently represented as an array of numbers representing the ratio of signal intensity at each point to the overall average, as shown at the bottom of FIG. 4 again for the magnified chamber 110b. Alternatively, other means such as color-coding or three-dimensional graphing may be used.

The results are conveniently represented as an array of numbers representing the ratio of signal intensity at each point to the overall average, as shown at the bottom of FIG. 4 again for the magnified chamber 110b. Alternatively, other means such as color-coding or three-dimensional graphing may be used.

As is shown by the grid in FIG. 4, the signal distribution with electrodes placed at the narrow ends of a rectangular chamber is typically quite uniform save in the small regions immediately adjacent to the electrodes themselves. Uniformity also improves with time, either in medium or in plain saline, as cut or broken oxide heals. The above-average readings at lower left in FIG. 4, for example, may have resulted from incompletely healed oxide at the cut wire end.

For convenience in handling, minimal medium evaporation and ease in maintaining sterility, all of the chambers, bridges and end wells in a group may conveniently be assembled on a rigid glass plate or other sterilizable carrier, and one of more of these plates once assembled may then be enclosed in an outer container such as a rigid plastic box.

The present invention also provides novel stimulation devices for delivering electrical signals in order to promote bone growth or repair. Specifically, novel passive electrode systems are provided for delivering electrical signals. These electrode systems couple time-varying electric signals for in vitro or in vivo applications; and replace conventional electrolyte bridge technology for the delivery of PEMF-type signals by induction in favor of a capacitive coupling. The electrode systems may be made of materials such as, but not limited to, anodized metals such as niobium, tantalum, titanium, zirconium, molybdenum, tungsten and vanadium. Aluminum and stainless steels share this property but to a much lesser degree, since they are slowly attacked by solutions containing chloride ion. At usable frequencies, typically between about 5 Hz and 3 MHz and, with circuit refinement, from below about 1 Hz to in excess of about 30 MHz, DC current passage is negligible.

Niobium is one of several metals that is self-passivating thereby forming thin but very durable surface oxide layers when exposed to oxygen and moisture. This process can be controlled by anodization. Generally self-passivation makes reliable connection with other methods difficult, however the present design uniquely uses capacitive coupling to induce a current in the electrode and thereby avoids the difficulty of forming electrical connections with other metals. This electrode system provides negligible electrolysis and no physiologically significant cytotoxicity and is also useful for in vivo applications.

The wires that are used with the electrode system of the present invention are "self-protecting," forming thin, but very durable and tightly adhering surface layers of non-reactive oxides when exposed to moisture or oxygen. The oxide so formed has a high dielectric constant, and the thickness of the oxide is substantially uniform and can be closely controlled. The protective oxide coating allows the metal to act as a coupling capacitor for introducing alternating current (zero net charge, or ZNC) electric signals to culture media with even distribution and negligible electrolysis.

A stimulator or other signal source, generally indicated by 100, is connected through wires, clip leads or by any other convenient means 102 to a pair of relatively inert metal electrodes 104a and 104b which are immersed in electrically conductive fluid in end wells 106a and 106b. These provide an entry point for the signal to the assembly of culture chambers 110a, 110b and so forth to which it is to be applied. Fine (99.9% pure) silver is preferred for electrodes 104a and 104b, and saline (sodium chloride solution) for the fluid in end wells 106a and 106b, since in use a thin layer of silver chloride forms at the interface and through a reversible electrochemical reaction facilitates the passage of electric current. Other metals and fluids, however, may also be used.

Bridges 112a, 112b and so forth may be formed of any relatively inert metal provided that it is not cytotoxic. Metals typically used as inert electrodes for biological fluids are silver, gold, platinum and the other platinum-group metals. Unfortunately these are very costly, may permit or even catalyze some electrochemical reactions at their surfaces (especially if minor impurities are present), and the products of such reactions may be cytotoxic.

For this reason the group of so-called "self-protecting" metals, which on contact with water or aqueous solutions form thin, continuous, highly insoluble and biologically inert surface oxide layers sealing the metal surface away from further fluid contact, are preferred in this invention. This oxide forms the only contact between the electrical signal delivery system and the culture medium. Such metals include niobium, tantalum, titanium, zirconium, molybdenum, tungsten and vanadium. Aluminum and stainless steels share this property but to a much lesser degree, since they are slowly attacked by solutions containing chloride ion (as nearly all biological fluids do).

Oxide formation on such a metal can be enhanced, and the oxide thickness increased in a closely controllable manner, through anodization. Uniform oxide thickness gives uniform capacitance per unit area of metal surface, in turn yielding relatively uniform signal intensity over the surface almost regardless of its shape in the fluid. Small breaks in the oxide, caused by cutting and forming, heal rapidly by further reaction with the fluid.

Niobium is preferred especially for this application since, thanks to the vivid and stable colors created by light interference in the surface oxide ($Nb_2O_5$) produced by anodization, it is popular in jewelry and thus available at reasonable cost in convenient forms and a variety of stock colors. Rio Grande Jeweler's Supply, for example, stocks 20- and 22-gauge round niobium wire pre-anodized to "purple," "pink," "dark blue," "teal," "green" and "gold," each color representing a different oxide thickness. The wire is easily worked and formed to any desired electrode shape. Given the refractive index of $Nb_2O_5$ ($N_D$=2.30) and its dielectric constant ($\epsilon_R$=41 $\epsilon_0$), the oxide thickness may be measured easily from the light reflection spectrum, and the resulting capacitance per unit of area or wire length may be calculated. "Purple" wire has the thinnest oxide, measured at 48 nM from the 420-nM peak reflectance, and thus for 22-gauge "purple" wire (0.0644 cm diameter; Rio Grande catalog number 638-240) the capacitance was calculated at 0.154 microfarad per centimeter of wire length. Direct measurement initially gave much higher readings due to oxide breaks, but after 24 hours in saline the measured capacitance had stabilized at 0.158 microfarad per centimeter, close to the predicted value.

Bridges 112a, 112b and so forth thus function electrically much as conventional salt bridges do, save that there is no possibility of fluid or ion flow through them, thus avoiding possible cross-contamination between chambers or between a chamber and an end well. In addition, the problems of evaporation and possible breakage encountered with conventional salt bridges, and the inconvenience of working with agar or other gelling agents, are avoided. Since they are electrically capacitive, the bridges block direct current and thus the signal reaching the chambers is charge-balanced between phases, with any direct-current component removed.

All bridge ends making contact with the growth medium preferably have the same approximate dimensions and contain roughly the same length of wire, so all have roughly equal capacitance, and are placed against the narrow ends of culture chambers which themselves are preferably rectangular, as shown in the magnified chamber 110b in FIG. 4. The bridge ends making contact with the fluid in the end wells (for example, the left ends of bridges 112a and 112g in FIG. 4) may if desired be given a different form to enhance contact, decrease capacitance, and/or better fit the size and shape of the end wells if these differ from the culture chambers. For example, when using round end wells the bridge ends immersed in them may conveniently be formed as spirals 144 as shown in FIG. 4.

Figure 2B:
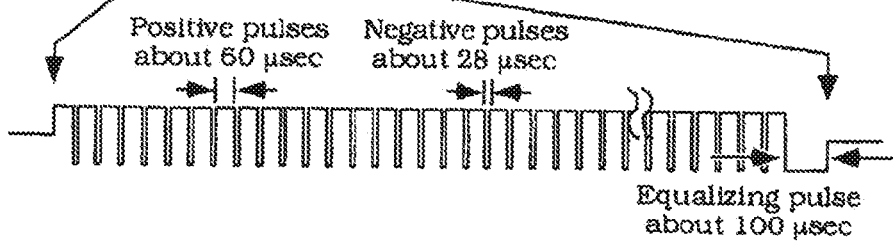

In summary therefore, the biological systems as contemplated by the present invention comprise the following elements: electrical simulators, anodized metal electrodes, and cells. Suitable PEMF signals for use in such systems include waveforms as described for example in FIG. 2 or 3. Practical applications of such signals include increasing proliferation, differentiation or mineralization of bone tissue, increasing BMP expression, or increasing nitric oxide production.

Tissue Engineering

The methods of the present invention may also be used in tissue engineering applications. Cells may be cultured using the methods and culture systems of the present invention in combination with biologically compatible scaffolds to generate functional tissues in vitro or ex vivo or transplanted to form functional tissues in vivo. Transplanted or host stem cells may also be selectively transplanted or attracted to a site of injury or disease and then stimulated with the electrical signals described herein to provide enhanced healing or recovery. Tissue scaffolds may be formed from biocompatible natural polymers, synthetic polymers, or combinations thereof, into a non-woven open celled matrix having a substantially open architecture, which provides sufficient space for cell infiltration in culture or in vivo while maintaining sufficient mechanical strength to withstand the contractile, compressive or tensile forces exerted by cells growing within the scaffold during integration of the scaffold into a target site within a host. Tissue scaffolds may be rigid structures for generating solid three-dimensional structures with a defined shape or alternatively, scaffolds may be semi-solid matrices for generating flexible tissues.

The methods and culture systems of the present invention include the use scaffolds made from polymers alone, copolymers, or blends thereof. The polymers may be biodegradable or biostable or combinations thereof. As used herein, "biodegradable" materials are those which contain bonds that may be cleaved under physiological conditions, including enzymatic or hydrolytic scission of the chemical bonds.

Suitable natural polymers include, but are not limited to, polysaccharides such as alginate, cellulose, dextran, pullane, polyhyaluronic acid, chitin, poly(3-hydroxyalkanoate), poly (3-hydroxyoctanoate) and poly(3-hydroxyfatty acid). Also contemplated within the invention are chemical derivatives of said natural polymers including substitutions and/or additions of chemical groups such as alkyl, alkylene, hydroxylations, oxidations, as well as other modifications familiar to those skilled in the art. The natural polymers may also be selected from proteins such as collagen, zein, casein, gelatin, gluten and serum albumen. Suitable synthetic polymers include, but are not limited to, polyphosphazenes, poly(vinyl alcohols), polyamides, polyester amides, poly(amino acids), polyanhydrides, polycarbonates, polyacrylates, polyalkylenes, polyalkylene glycols, polyalkylene oxides, polyalkylene terephthalates, polyortho esters, polyvinyl ethers, polyvinyl esters, polyvinyl halides, polyesters, polylactides, polyglyxolides, polysiloxanes, polycaprolactones, polyhydroxybutrates, polyurethanes, styrene isobutyl styrene block polymer (SIBS), and copolymers and combinations thereof.

Biodegradable synthetic polymers are preferred and include, but are not limited to, poly α-hydroxy acids such as poly L-lactic acid (PLA), polyglycolic acid (PGA) and copolymers thereof (i.e., poly D,L-lactic co-glycolic acid (PLGA)), and hyaluronic acid. Poly α-hydroxy acids are approved by the FDA for human clinical use. It should be noted that certain polymers, including the polysaccharides and hyaluronic acid, are water soluble. When using water soluble polymers it is important to render these polymers partially water insoluble by chemical modification, for example, by use of a cross linker.

One of the advantages of a biodegradable polymeric matrix is that angiogenic and other bioactive compounds can be incorporated directly into the matrix so that they are slowly released as the matrix degrades in vivo. As the cell-polymer structure is vascularized and the structure degrades, the cells will differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), EGF, and HB-EGF, could be incorporated into the matrix or provided in conjunction with the matrix. Similarly, polymers containing peptides such as the attachment peptide RGD (Arg-Gly-AsP) can be synthesized for use in forming matrices.

Kits

Kits are also provided in the present invention that combine electrical stimulators with biologically compatible scaffolds to support the growth and integration of cells into a unified tissue. Containers with built in electrodes may be provided with the kit and the electrodes may be made of a self-passivating material or other conventional electrode materials. These kits may optionally include reagents such as growth media, and growth factors to promote integration of the cells with the scaffolds. Scaffolds included in the kit may be designed to have growth-promoting and adhesion molecules fixed to their surface. Such kits are optionally packaged together with instructions on proper use and optimization.

Cells may be provided with the kit in a preserved form with a protective material until such time that the cells are combined with other elements of the kit to produce an appropriate tissue. In one embodiment, cells are provided that are cryopreserved in liquid nitrogen or dessicated in the presence of a compound such as trehalose. Cells may be undifferentiated progenitor cells, including stem cells; pluripotent stem cells, multipotent stem cells or committed progenitors. Alternatively, terminally differentiated cells may also be used with these kits. Such kits may be designed to produce replacement tissue for use in any organ system such as, but not limited to bone, cartilage, muscle, kidney, liver, nervous system, lung, heart, vascular system etc.

Cells may also be harvested from a patient in need of treatment to engineer replacement tissue from the patient's own tissue. Use of the patient's own tissue provides a way to produce transplantation tissue with reduced complications associated with tissue rejection.

In addition to purely electrical stimulation, a combination of electrical and mechanical stimulation in vitro may be found beneficial for some purposes. Mechanical stimulation may consist of tensile loading, compressive loading, or shear loading. Typical setups are shown in cross-section in FIGS. 8a through 8e.

In each case of loading, the test setup is built around a culture well or chamber 200 of any type familiar in the art, containing medium 202 and a layer of cells 204 typically attached to a bottom sheet or membrane 206 which may or not be a part of the rigid mechanical bottom 208 of the culture well. Electrodes 210, of any useable metal as described inter alia but preferably of a self-protecting metal and more preferably of anodized niobium, are placed in chamber 200 in such a way as to create relatively uniform current distribution throughout medium 202.

Figure 8A:
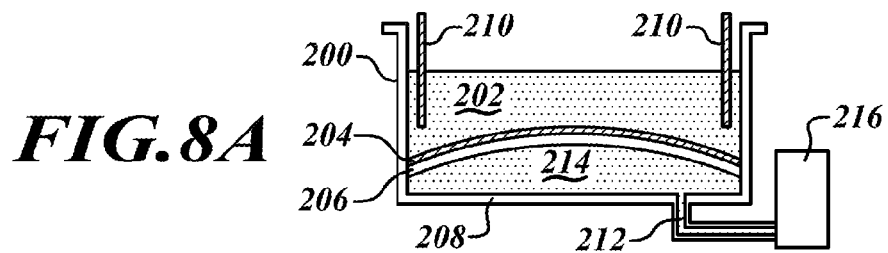
FIG. 8A provides an illustrative schematic setup for using a combination of mechanical and electrical stimulation for in vitro applications that includes a flexible membrane as a false bottom.

For tensile loading, membrane 206 forms an additional or "false" bottom in culture well or chamber 200 as shown in FIG. 8a. Membrane 206 may be made from any suitably flexible and elastic material to which the cells will attach themselves, such as silicone rubber which has been plasma etched. Tube 212 connects space 214 between membrane 206 and rigid chamber bottom 208 with an external pump or other source of steady or fluctuating pressure or vacuum 216. The intermittent operation of pressure or vacuum source 216 causes membrane 206 to flex up and down, creating intermittent tension in the membrane and thus in cell layer 204 attached to it. Alternatively, source 216 may apply little or no pressure across membrane 206 for an extended period, allowing cells 204 to colonize the membrane in its unstretched state, then apply a different pressure thereby stretching membrane 206, for example at a point in culture growth at which cells 204 have just reached confluence and established gap junction contact.

Figure 8B:
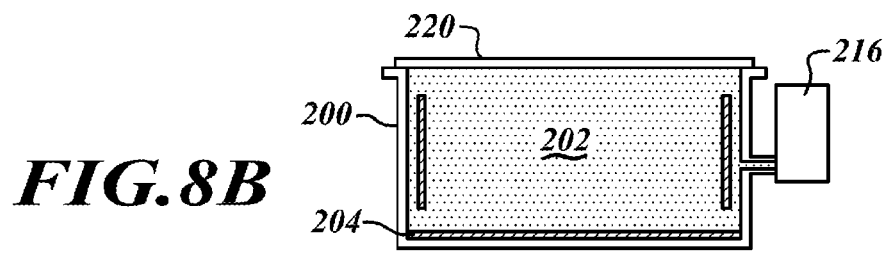
FIG. 8B provides an illustrative schematic setup for using a combination of mechanical and electrical stimulation for in vitro applications that includes a sealed cover and operably coupled pressure source.

For compressive loading, culture well or chamber 200 is instead sealed with a cover 220 and connected to pressure source 216 directly as shown in FIG. 8b. Source 216 creates a steady or fluctuating hydrostatic pressure in medium 202 which is thus applied directly to cell layer 204.

Figure 8C:
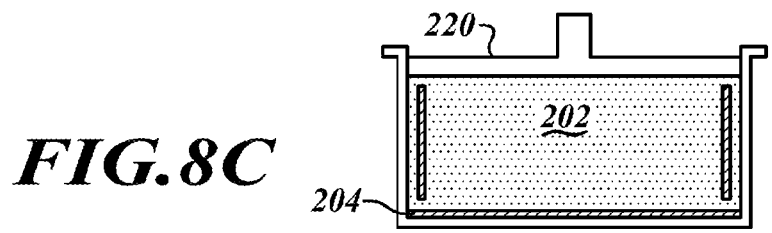
FIG. 8C provides an illustrative schematic setup for using a combination of mechanical and electrical stimulation for in vitro applications that includes a piston to apply pressure to a culture well.

As an alternative means for compressive loading, tube 212 and pressure source 216 are eliminated and chamber cover 220 takes the form of a movable piston through which steady or fluctuating pressure may be applied directly to medium 202 and thus to cells 204, as shown in FIG. 8c.

Figure 8D:
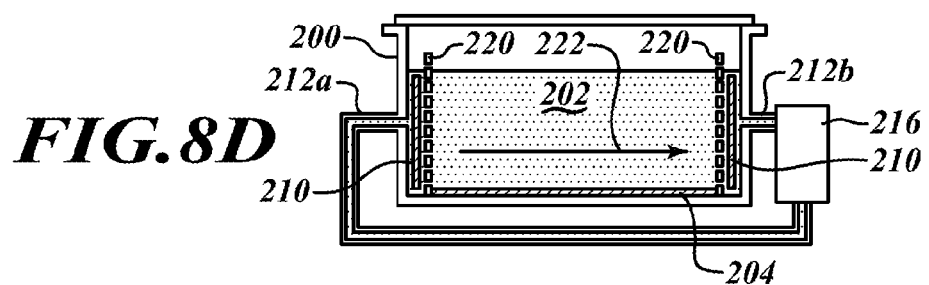
FIG. 8D provides an illustrative schematic setup for using a combination of mechanical and electrical stimulation for in vitro applications that includes a pressure source.

For shear loading, culture well 200 is connected to pressure source 216 instead via two tubes 212a and 212b through which medium 202 is circulated, as shown in FIG. 8d. This flow may be either constant in a single direction, intermittent, or oscillatory. Each tube is preferably equipped with baffles 220 to achieve more uniform flow, as generally indicated by arrow 222. Baffles 220 may be made separate from electrodes 210 as shown, or alternatively the electrodes may be perforated or otherwise made discontinuous so as themselves to form baffles. The motion of medium 202 and its friction against cell layer 204 generate the desired shear loading.

Figure 8E:
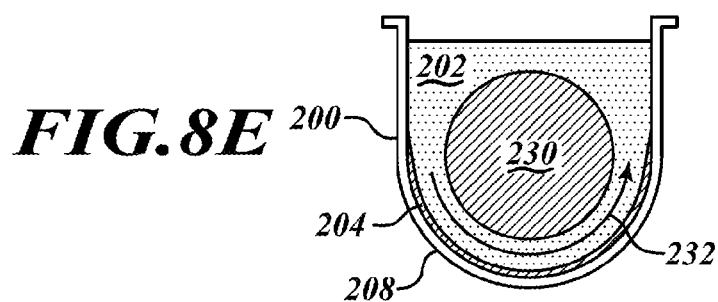
FIG. 8E provides an illustrative schematic setup for using a combination of mechanical and electrical stimulation for in vitro applications that includes a pressure source and impeller.

As an alternative means for providing shear loading, tubes 212a and 212b and pressure source 216 are replaced with a moving impeller 230 which maintains medium 202 in motion relative to cell layer 204 as generally indicated by arrow 232. Impeller 230 may take any of several forms, but may advantageously be of cylindrical form as shown in FIG. 8e, where the rigid bottom 208 of chamber 200 approximates the same form and maintains a relatively uniform clearance from the impeller surface. Medium 202 is thereby swept continuously and at a steady speed over cells 204 simply by maintaining impeller 230 in rotation at a constant speed. Alternatively, changing the speed of impeller 230 will change the flow velocity and thus the level of shear loading. Electrodes 210 are not shown since they may take a variety of positions in this arrangement. Preferably, however, rigid cell floor 208 and impeller 230 are themselves made of suitable electrode metals, more preferably of self-protecting metals and most preferably of anodized niobium, and themselves function as the electrodes.

Differential Modulation of Bone Growth

The waveforms of the present invention as described above are also useful in methods for promoting the growth and repair of bone tissue in vivo. As described above, stimulation with A-type waveforms promotes proliferation of cells. A-type waveforms also result in an increase in bone morphogenic proteins to promote differentiation. In one embodiment, an increase in BMP-2 and BMP-7 production is effected using A-type or to a lesser degree, B-type electrical signals. This effect is highly valuable and provides a method for enhancing the generation of sufficient tissue for proper tissue healing in vivo, or to creating tissue grafts. This signal is also valuable for providing sufficient cell mass for infiltration into a polymer scaffold for tissue engineering purposes. In another embodiment, as demonstrated by in vitro testing, stimulation in vivo provides proliferation and differentiation of osteoblasts to increase the number of osteoblasts for mineralization. Such an increase in number of cells provides a method for filling in gaps or holes in developing or regenerating bone through electrical stimulation. Cells generated through proliferation induced by A-type waveforms may be used immediately, or preserved using conventional cell preservation methods until a future need arises.

Stimulation with B-type waveforms promotes proliferation to a small degree, and has actions different than A-type waveforms. Actions promoted by B-type waveforms include, but are not limited to mineralization, extracellular protein production, and matrix organization. The actions of B-type waveforms are also valuable and provide methods to enhance the mineralization step and ossification of new bone tissue. In one embodiment, developing or regenerating bone tissue is stimulated with B-type waveforms to enhance the rate of mineralization. It has been proposed that B-type waveforms may act through calcium/calmodulin pathways and also by stimulation of G-protein coupled receptors or mechanoreceptors on bone cells. (Bowler, *Front Biosci*, 1998, 3:d769-780; Baribault et al., *Mol Cell Biol*, 2006, 26(2):709-717). As such, methods are also provided to modulate the activity of calcium/calmodulin-mediated actions as well as G protein coupled receptors and mechanoreceptors using electrical stimulation. Modulation of these cellular pathways and receptors are valuable to promote the growth and repair of bone tissue in vitro or in vivo.

Stimulation with C-type waveforms promotes bone regeneration, maturation and calcification. These waveforms are also valuable and provide methods to enhance the mineralization step and ossification of new bone tissue.

Stimulation using D-type waveforms promotes cartilage development and healing and bone calcification, and is useful for treating or reversing osteoporosis and osteoarthritis. Applications of these waveforms include in vivo applications such as repairing damaged cartilage, increasing bone density in patients with osteoporosis as well as in vitro applications relating to the tissue engineering of cartilage for example.

Methods are also provided for combination or sequential use of the waveforms described herein for the development of a treatment regime to effect specific biological results on developing or regenerating osteochondral tissue.

In one embodiment, fractures in patients with a bone disorder may be treated with signals to heal fractures and then strengthen the bone. As a non-limiting example of this embodiment, an osteoporotic patient with a fracture may be treated by first stimulating with an A-type signal to promote proliferation and release of growth factors and then a B-type waveform to promote an increase in bone density at the site of repair to increase bone mass density and prevent refracture.

In another embodiment, combining two or more types of waveforms described herein may be used to promote the sequential proliferation, differentiation and mineralization of osteochondral tissues. As a non-limiting example of this embodiment, a culture of osteoblasts may be grown under the influence of a A-type signal in connection with or prior to connection with a polymeric matrix. After seeding the polymeric matrix, B-type signals are then administered to the cell-matrix construct to promote mineralization of a construct useful as a bone graft.

In a third embodiment, two or more signals may be administered simultaneously to promote concomitant proliferation, differentiation and mineralization of osteochondral tissue in vivo or in vitro. Different signals may also be applied sequentially to osteochondral tissue in order to yield a greater effect than delivering either signal alone. The sequential process may be repeated as needed to produce additional tissue (such as bone) by cycling through the two-step process enough times to obtain the desired biological effect. As a specific non-limiting example, A-type signals may be applied first to produce more bone cells by proliferation and then B-type signals may be applied to induce the larger number of bone cells to produce more bone tissue (matrix, mineral and organization) and then repeated if needed. The amount of bone produced using repetition of a sequential stimulation protocol would be greater than that produced by either signal alone or in combination.

Progenitor Cell Timulation

The methods and waveforms described herein may be applied to undifferentiated precursor cells to promote proliferation and/or differentiation into committed lineages. Such progenitor cells may include, but are not limited to, stem cells, uncommitted progenitors, committed progenitor cells, multipotent progenitors, pluripotent progenitors or cells at other stages of differentiation. Also included are specifically osteoblasts and chondroblasts. In one embodiment, multipotent adult stem cells (mesenchymal stem cells or bone marrow stem cells) are stimulated with A-type signals in vitro to promote proliferation and differentiation of the multipotent adult stem cells into specific pathways such as bone, connective tissues, fat etc. Combination or sequential administration with both signals is also contemplated for progenitor cell stimulation as previously described.

Alternatively, the waveforms and methods described herein may also be applied to multipotent adult stem cells (mesenchymal stem cells or bone marrow stem cells) in vivo to stimulate cells with A-type signals to promote proliferation and differentiation of the multipotent adult stem cells into specific pathways such as bone, connective tissues, fat etc. Combination or sequential administration with both signals is also contemplated.

Electrical stimulation of progenitor cells may also be accompanied by proliferation and differentiation factors known to promote proliferation or differentiation of progenitor cells. Proliferation factors include any compound with mitogenic actions on cells. Such proliferation factors may include, but are not limited to bFGF, EGF, granulocyte-colony stimulating factor, IGF-I, and the like. Differentiation factors include any compound with differentiating actions on cells. Such differentiation factors may include, but are not limited to retinoic acid, BMP-2, BMP-7 and the like.

The electrical waveforms described herein provide differential and combination modulation on the growth and development of osteochondral tissue in vitro or in vivo. Increasing the proliferation of cells with A-type signals before mineralization increases the number of bone cells and therefore provides an increase in the subsequent mineralization effected by stimulation with B-type signals. The waveforms of the present invention also promote proliferation and differentiation of progenitor cells through the release of nitric oxide and bone morphogenic proteins.

Capacitive Coupling

Stimulation of in vitro and in vivo preparations is often difficult with self-passivating metals because it is difficult to obtain electrical connections between metals. The present invention provides methods of obtaining the benefits of using self-passivating metal electrodes without problems associated with obtaining solid electrical connections. Capacitive coupling of these electrodes provides a method to induce direct current through the self-passivating metal electrode circumventing the need for any electrical connection. In this method electrodes made from self-passivating metals such as niobium, tantalum, titanium, zirconium, molybdenum, tungsten and vanadium, aluminum and stainless steels are sterilized and placed in close proximity to a population of cells to be stimulated. Circuit wires are placed within close proximity to the metal electrodes in a conductive medium such as saline solution and electrical signals are transmitted through the circuit wires with current being capacitively coupled from the wire through the saline and the oxide layer into the self-passivating metal electrode to thereby stimulate the cell population. In one embodiment, capacitive coupling stimulation is used for in vitro applications such as, but not limited to, cell culture. One culture dish may be stimulated using this method or several culture dishes or wells may be linked together for uniform electrical stimulation.

In another embodiment, capacitive coupling stimulation is used for in vivo applications where a sterile anodized metal electrode is implanted into a patient in need of treatment and the circuit wires are placed outside the patient in contact with the skin to induce a current in the implanted metal electrode for an effective amount of time to promote repair or growth of a tissue. For example, the outer end of the electrode may form a flat coil just beneath the skin and the signal may be coupled into it using a conventional skin contact electrode, placed on the skin directly over this coil. Portions of the capacitivley coupled electrode from which close capacitive coupling to tissues is not desired may be covered with any insulating material suitable for use in implanted circuits, as is well known in the art, thus minimizing signal loss and undesired stimulation of tissues not being treated. In a specific example such as bone repair, a sterile anodized metal electrode made from a self-passivating metal is implanted into a patient in need of treatment and stimulated. After a sufficient period of time for repair of the bone, the electrode may be removed from the patient.

Increase BMP Expression

The present invention further includes methods and apparatuses that use A-type and B-type waveforms for promoting the expression and release of bone morphogenic proteins (BMPs) from stimulated cells. The electrical signals described herein may be used to cause the release of BMPs at levels sufficient to induce a benefit to the tissues exposed to the signals. Benefit may occur in tissues not directly exposed to the signals.

BMPs are polypeptides involved in osteoinduction. They are members of the transforming growth factor-beta superfamily with the exception of the BMP-1. At least 20 BMPs have been identified and studied to date, but only BMP 2, 4 and 7 have been able in vitro to stimulate the entire process of stem cell differentiation into osteoblastic mature cells. Current research is trying to develop methods to deliver BMPs for orthopedic tissue regeneration. (Seeherman, *Cytokine Growth Factor Rev.* 2005 June; 16(3):329-45). Methods are provided herein to induce the release of BMPs in vitro or in vivo for orthopedic tissue regeneration through electrical stimulation instead of through delivery of exogenous BMPs in technically demanding and costly delivery methods.

In one embodiment, A-type and to a lesser degree, B-type waveforms are used to induce expression and release of endogenous BMPs. Release of endogenous BMPs promotes the growth and differentiation of target tissues. Placement of stimulation electrodes provides a way to target BMP expression to localized areas of an in vitro preparation or in vivo in a patient in need of increased BMP expression. In one embodiment, BMP-2 or BMP-7 or combinations thereof are released endogenously to effect differentiation and growth of target tissue. In a specific embodiment, release of either or both of BUT-2 and BMP-7 promotes differentiation, mineralization, protein production and matrix organization in bone or cartilage tissue.

Stimulation of Bone, Cartilage or Other Connective Tissue Cells by Nitric Oxide

The methods and electrical signals described herein may also be used to promote repair and growth of bone, cartilage or other connective tissues. In one embodiment, a B-type waveform increases the growth of cells through the release of nitric oxide (NO). The waveforms may cause the release of nitric oxide at levels sufficient to induce a benefit to the tissues exposed to the signals. Benefit may occur in tissues not directly exposed to the signals. Bone, cartilage, or other connective tissue cell growth may be increased further by co-administration of an NO donor in combination with the electrical stimulation. NO donors include but are not limited to sodium nitroprusside (SNP), SIN-I, SNAP, DEA/NO and SPER/NO. Bone, cartilage, or other connective tissue cell growth may be reduced by co-administering an NO synthase inhibitor in combination with the electrical stimulation. Such NO synthase inhibitors include but are not limited to N(G)-nitro-1-arginine methyl ester (L-NAME), NG-monomethyl-L-arginine (L-NMMA), and 7-Nitroindazole (7-NI). Using these methods, bone, cartilage, or other connective tissue cell growth may be modulated depending on specific needs.

Application of the Apparatus and Methods of the Present Invention

By using the apparatus and methods of the present invention as described herein, the apparatus and methods are effective in promoting the growth, differentiation, development and mineralization of osteochondral tissue.

The apparatus is believed to operate directly at the treatment site by enhancing the release of chemical factors such as cytokines which are involved in cellular responses to various physiological conditions. This results in increased blood flow and inhibits further inflammation at the treatment site, thereby enhancing the body's inherent healing processes.

The present invention is especially used in accelerating healing of simple or complex (multiple or comminuted) bone fractures including, but not limited to, bones sawed or broken during surgery. The present invention can be used to promote fusion of vertebrae after spinal fusion surgery.

The present invention may be used to treat nonunion fractures; treat, prevent or reverse osteoporosis; treat, prevent or reverse osteopenia; treat, prevent or reverse osteonecrosis; retard or reverse formation of woven bone (callus, bone spurs), retard or reverse bone calcium loss in prolonged bed rest, retard or reverse bone calcium loss in microgravity. In addition, the present invention may be used to increase local blood circulation, increase blood flow to areas of traumatic injury, increase blood flow to areas of chronic skin ulcers and to modulate blood clotting.

One of the areas where the present invention can also be used is to accelerate the healing of damaged or torn cartilage. Also, the present invention can be used to accelerate the healing (epithelialization) of skin wounds or ulcers.

The present invention may further be used to accelerate growth of cultured cells or tissues, modulate cell proliferation, modulate cell differentiation, modulate cell cycle progression, modulate the expression of transforming growth factors, modulate the expression of bone morphogenetic proteins, modulate the expression of cartilage growth factors, modulate the expression of insulin-like growth factors, modulate the expression of fibroblast growth factors, modulate the expression of tumor necrosis factors, modulate the expression of interleukines and modulate the expression of cytokines.

The methods and apparatuses of the present invention are further illustrated by the following non-limiting examples. Resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Effect of PEMF Signal Configuration on Mineralization and Morphology in a Primary Osteoblast Culture The goal of this study was to compare two PEMF waveform configurations delivered with capacitative coupling by evaluating biochemical and morphologic variations in a primary bone cell culture.

Methods

Osteoblast cell culture: Primary human osteoblasts (CAMBREX®, Walkersville, Md.) were expanded to 75% confluence, and plated at a density of 50,000 cells/ml directly into the LAB-TEK™ (NALGE NUNC INTERNATIONAL™, Rochester, N.Y.) chambers described previously. Cultures were supported initially with basic osteoblast media without differentiation factors. When the cultures reached 70% confluence within the chambers, media was supplemented with hydrocortisone-21-hemi succinate (200 mM final concentration), β-glycerophosphate (10 mM final concentration), and ascorbic acid. Osteoblasts were incubated in humidified air at 37° C., 5% $CO_2$, 95% air for up 21 days. Media was changed every two days for the course of the experiment, 4 ml supplementing each chamber.

Electrical Stimulation: Cultures were stimulated for either 30 minutes or for 2 hours twice per day. Two electrical signal regimens were selectively applied to the cells, one a continuous waveform indicated as "Signal A" (60/28 positive/negative signal duration in μsec), and the other a continuous waveform indicated as "Signal B" (200/28 positive/negative signal duration in μsec). Intensity was measured in sample runs as 2.4 mV/cm (peak to peak). Non-stimulated osteoblasts (NC) were plated at identical densities (as controls) in a similar manner. The following were measured using procedures in Detailed Methods: alkaline phosphatase, calcium, osteocalcin, and histology. Each of the following graphs are keyed to the "A" signal, the "B" signal, 30-minutes duration as "1", 2-hours duration as "2", and NC (or confluence) as no current (i.e. A1 would be A signal—30 minutes; B2 would be B—2 hours).

The electrical device used herein enables the application of continuous waveform, electrical stimulation to multiple explants simultaneously. For each experiment, 6 pairs of explants were placed into individual wells in 4 ml of culture medium. Control specimens were cultured in similar conditions, the only difference being the lack of signal delivered. The present test configuration consisted of six test culture wells (17×42 mm) connected in series via a coiled section of niobium wire.

Human osteoblast cells were established in LAB-TEK™ II slide wells (NALGE NUNC INTERNATIONAL™, Rochester, N.Y.), each with a surface area of about 10 $cm_2$. Signals were applied to several chambers simultaneously by connecting them in serial via niobium wires which acted as a couple capacitance. The stimulus was either a 9 msec burst of 200/28 μsec bipolar rectangular pulses repeating at 15/sec, delivering 9 mV/cm (similar to the standard clinical bone healing signal), designated Signal B, or a 48 msec burst of 60/28 μsec essentially unipolar pulses delivering 4 mV/cm, designated Signal A. Cultures received either a 30-minutes or a 2-hour stimulus twice a day. Samples were taken from the media and analyzed at 7, 14, and 21 day time points for alkaline phosphatase, osteocalcin, matrix calcium and histology. Mineralization accompanying morphology was confirmed with Von Kossa stain. All biochemical analyses were performed by conventional assay techniques.

Results $PGE_2$, production was assessed using commercially available ELISA kits (R&D SYSTEMS™, Minneapolis Minn.; INVITROGEN, INC.™, Carlsbad, Calif.). Results are expressed as pg/mg of tissue per 24 hours (μM/g/24 hrs).

Figure 5:
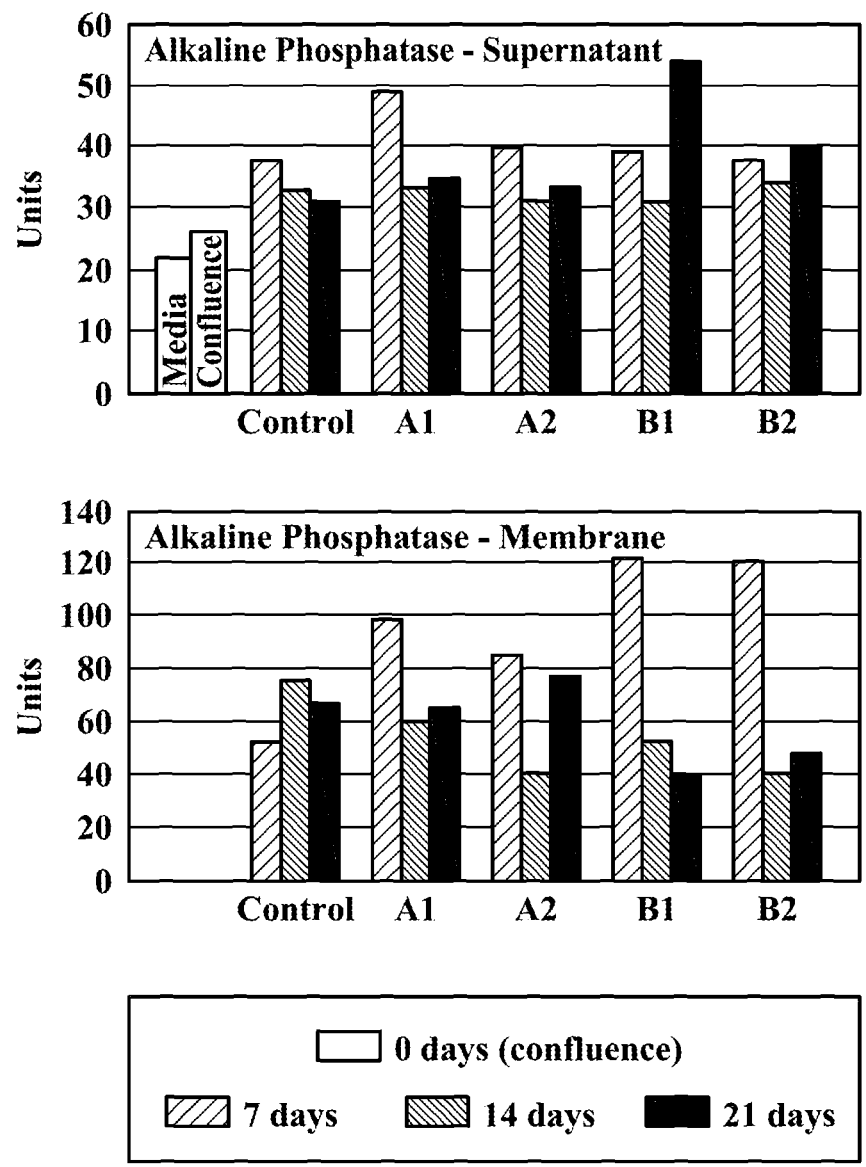
FIG. 5 provides a bar graph showing the changes in alkaline phosphatase in supernatant (left), and in membrane (right).

Alkaline Phosphatase (AP): At the time points indicated in the study design, cells were lysed (Mammalian-PE, Genotech, St. Louis, Mo.) and the supernatant collected. Alkaline phosphatase was measured by the cleavage of para-nitrophenyl phosphate (PNPP) to nitrophenyl (PNP) under basic conditions in the presence of magnesium. The end product PNP is colorimetric with an obsorption peak at 405 nanometers. Basic conditions were achieved using 0.5 M carbonate buffer at pH 10.3. Culture media was assayed directly for ALP activity. Cell layer ALP was extracted with a solution of triton X-100 and an aliquot measured for ALP activity. Alkaline Phosphatase was measured in both the supernatant and in the membrane following lysis buffer extraction (FIG. 5). As expected from other studies (Lohman, 2003), alkaline phosphatase expression peaked near 7 days in the membrane. In the cells cultured under the "B" stimulus however, culture media continued to demonstrate an increase in measurable AP.

Figure 6:
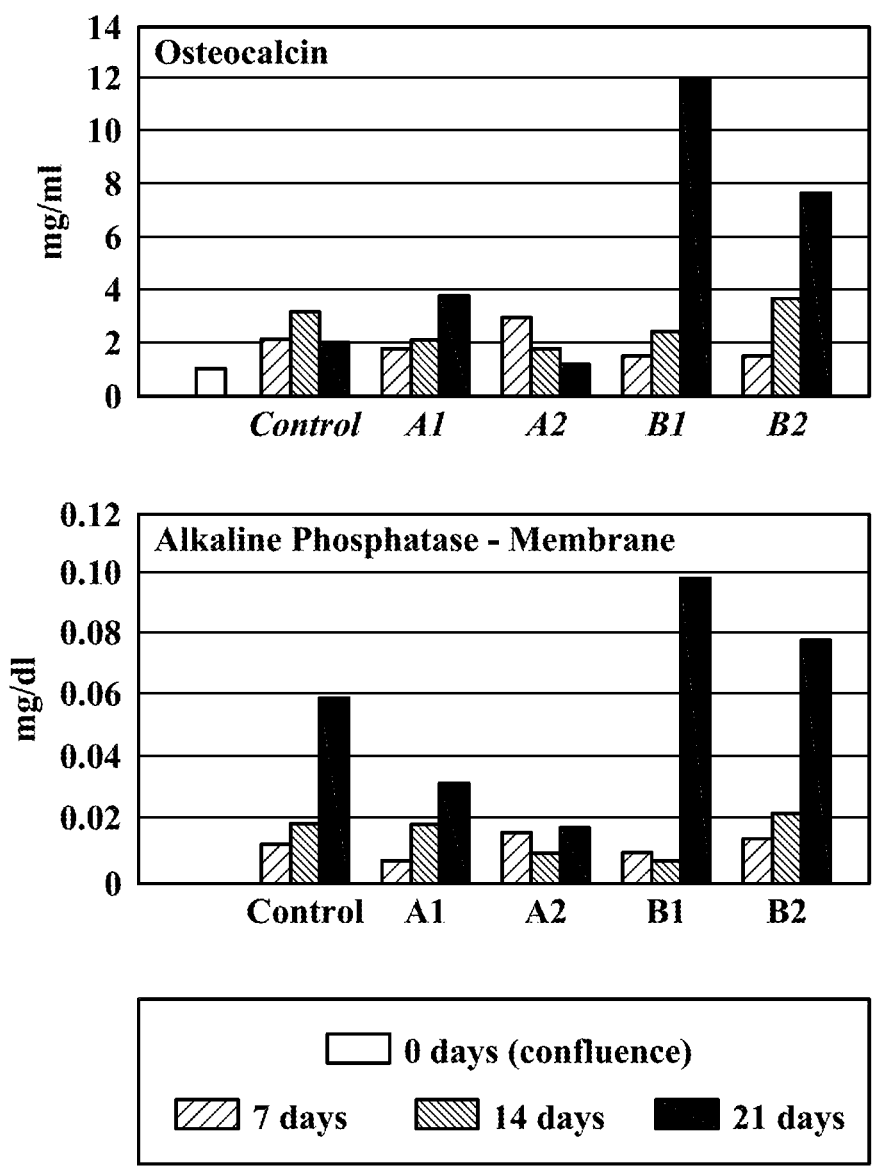
FIG. 6 provides a bar graph showing the changes in osteocalcin and calcium deposits with signal "B".

Osteocalcin: Osteocalcin (5800 daltons) is a specific product of the osteoblast. A small amount of osteocalcin is released directly into the circulation; it is primarily deposited into the bone matrix. Studies have shown that osteocalcin circulates both as the intact (1-49) protein and as N-terminal fragments. The major N-terminal fragment is the peptide (1-43). A Mid-Tact Osteocalcin Elisa Kit was selected for its high specificity. The assay is highly sensitive (0.5 ng/ml) and required only a 25 microliter sample. Standards run simultaneously with our experimental groups offered a strong correlation to the expected values provided by BTI manufacturers (BTI, Stoughton, Mass.). Osteocalcin deposition, measured subsequent to quenching the cultures and determined from the matrix component, was more pronounced following the "B" stimulus and highest at 21 days (FIG. 6).

DNA content: Cell layer was extracted with 0.1 N sodium hydroxide and an aliquot assayed for DNA content using CyQuant assay kit (INVITROGEN, INC.™, Carlsbad, Calif.). For cell samples extracted for ALP content with triton X-100 the extract was adjusted to 0.1N sodium hydroxide using 1 N sodium hydroxide. Standard curves contain matching buffer. For samples also requiring protein content an aliquot was measured for protein using dye binding method (Bradford).

Calcium: Calcium was determined by Schwarzenbach methodology with o-cresolphthalein complexone, which forms a violet colored complex. By adding 2 ml of 0.5 M acetic acid overnight, calcium was dissolved and content was quantified against standards by colorimetric assay at 552 nm (CORE LABORATORY SUPPLIES™, Canton, Mich.).

Calcium Distribution in the culture was also assessed by histology. Cells were fixed in 2% glutaraldehyde, washed with cacodylate buffer, washed with PBS and then hydrated for staining as indicated. Each time period was run in tandem; representative morphology is presented for 21 days, comparing the "A" signal, with the "B" signal, and comparing both signals to the control (FIG. 6). For signal B, the most striking observation was in the distribution of the calcium with an apparent preferential alignment that we interpreted as a "pseudo-cancellous" bone. For signal A, there appeared to be qualitatively more cell proliferation and less matrix production than signal B (however, signal A clearly had more matrix than with controls).

Osteometric analysis was developed and modified from the methodology of Croucher. In this two dimensional chamber system, mean trabecular area relative to total area of the grid sampled was studied. Using minimum of 20 fields from two chambers at each intensity, the study examined bone formation, osteoid width, and cell number. Random specific grids were developed for direct comparison and to remove bias. Additionally, osteoblast cultures in both stimulated and control chambers was stained directly by VonKossa method (Mallory, 1961) to examine histology and qualify the distribution of calcium within the cultures.

Conclusion

Alkaline phosphatase, which rose to a peak near the 10-14 day level and then gradually subsided, was increased in the supernatant stimulated by Signal B. Osteocalcin deposition, measured subsequent to quenching the cultures and determined from the matrix component, was more pronounced following Signal B only and increased to its highest point at 21 days. Matrix calcium measured in mg/dl, and matrix calcium as a function of the area of the tissue culture plate were greatest with Signal B only. Mineral distribution as noted by histology and Von Kossa staining validated the biochemical data from the assays. The B stimulus conferred a greater amount of mineral, and moreover suggested a reticulated 2-dimensional pattern that may offer analogous tension dynamics as would be expected in a 3-D trabecular array. Cell proliferation appeared qualitatively higher with Signal A vs control, whereas significantly increased mineralization and pattern was apparent at 21 days with Signal B.

That the two signal configuration produced very different effects is readily explainable by a signal to noise ratio (SNR) analysis which showed the delectability of signal B was 10× higher than signal A, assuming a Ca/CaM target. This study demonstrates for the first time that PEMF has the potential to effect structural changed resonant with tissue morphology. The geometric pattern apparent at 21 days of culture, mirrored the trabecular reticulation consonant with cancellous bone and starkly contrasted the random orientation of the cells in both the control and the cultures exposed to signal A at all time points evaluated. Such outcomes suggest that preferred signal configurations can effect structural hierarchies that previously were confined to tissue-level observations.

Example 2

Use of a Niobium "Salt" Bridge for In Vitro PEMF Stimulation

Introduction

A passive electrode system using anodized niobium wire was developed to couple time-varying electric signals into culture chambers. The intent of the design was to reduce complexity and improve reproducibility by replacing conventional electrolyte bridge technology for delivery of PEMF-type signals, such as those induced in tissue by the EBI repetitive pulse burst bone grown stimulator, capacitively rather than inductively, in vitro for cellular, tissue studies. Anodized niobium wire is readily available and requires only simple hand tools to form the electrode bridge. At usable frequencies, typically between 5 Hz and 3 MHz, DC current passage is negligible.

Background

Capacitively-coupled electric fields have typically been introduced to culture media with conventional electrolyte salt bridges which have limited frequency response and are difficult to use without risk of contamination for extended exposure times. Niobium (columbium) is one of several metals which are self-passivating, forming thin but very durable surface oxide layers when exposed to oxygen or moisture. Others are tantalum, titanium, and to a much lesser degree, stainless steels. The process can be accelerated and controlled by anodization. A problem with self-passivation is that it makes reliable connection with other metals difficult. The present design avoids that difficulty.

Materials and Methods.

Niobium oxide, $Nb_2O_5$, is hard, transparent, electrically insulating and inert to water, common reagents and biological fluids over a wide pH range. Anodizing niobium forms $Nb_2O_5$ with uniform thickness, showing a range of vivid light-interference colors valued for jewelry since no dye is added, and yields stable and reproducible capacitances. Jeweler's niobium is sold in standard colors each representing a different oxide thickness. Since the dielectric contact of $Nb_2O_5$ is unusually high ($\epsilon_R=41\epsilon_0$) and the layers are thin (48-70 nm), their capacitances are surprisingly large. "Purple" niobium has the thinnest oxide and highest measures capacitance: 0.158 µF/cm for 22-gauge wire (Rio Grande #638-240), near the calculated value for 48 nM oxide (420 nM peak reflectance). In water or physiological salines, cut wire ends and small flaws formed in bending quickly heal over with oxide, with no need for re-anodization.

The Niobium Bridge:

In this application niobium oxide forms the only electrical contact with the medium and PEMF-type signals pass thought it capacitively. At signal levels below a few milliamperes, there is negligible electrolysis or pH change to cause artifacts. Multiple chambers may be joined in series, each receiving identical signals. Each niobium bridge is bent forming a sheet-like electrode at each end, with a typical capacitance of 0.56 g. Placing electrode bridges at the ends of a rectangular chamber creates nearly uniform current distribution and voltage gradients throughout the medium. Gradients measured in a typical setup of culture changer, electrodes and PEMF-type signal as was previously shown in FIG. 4 and described in the accompanying text, show a mean variation of ±3%, mainly near electrodes or where the medium varies significantly in depth. A chamber or several joined in series are energized through special niobium end bridges, each with its outer end coupled capacitively through saline to a silver strip electrode forming a connection terminal. This removes any need to connect niobium to itself or to any other metal. Current is controlled by a series limiting resistance $R_{lim}$. The resulting bandpass (±3 dB of nominal) varies somewhat with $R_{lim}$, but in a test setup ran from 5 Hz to 3 MHz, the highest frequency tried. PEMF-type signals can thus be delivered undistorted in vitro via capacitive coupling.

Experimental:

The utility of the niobium electrode bridge was tested on osteoblast and chondrocyte cultures using a B-type waveform as previously described. With this signal applied to OGM™ osteoblast medium (CAMIBREX®, Walkersville, Md.) without cells present, the measured pH after 24 hours was 8.29 compared with 8.27 in non-energized controls, suggesting negligible electrolysis. Absence of physiologically significant cytotoxicity was shown by robust proliferation of osteoblasts, differentiation and development of a cancellous bone-like structure over 21 days in OGM™ using both A-type and B-type waveforms, After 30 minute and 2 hour exposure for 21 days to the waveform in culture, cells and matrix were analyzed with energy-dispersive X-ray (EDX). No niobium could be detected. In other studies a B-type signal was applied to human cartilage cells (HCC) in culture medium containing 1% fetal calf serum for 96 hours. The B-type signal caused a 154% increase in cell number as measure by DNA content of cell lawyer, again showing no significant cytotoxicity. In a direct comparison between the capacitively coupled signal and an otherwise identical but electromagnetically coupled signal, each delivered 30 minutes daily for four days, measured increases in osteoblast number by DNA differed significantly from controls (157% for niobium, 164% for EM coupled) but not from each other.

Conclusions.

A novel niobium electrode bridge has been developed to apply capacitively coupled PEMF-type signals to cells/tissues in culture. The bandpass of the niobium bridge is 5 Hz to 3 MHz, so PEMF-type signals like those used clinically for bone and wound repair pass without distortion. Unlike standard electrolyte bridge configurations, the niobium bridge provides uniform current density within the culture dish. Application for extended PEMF exposures shows no electrolysis or physiologically significant cytotoxicity.

Example 3

Stimulation of Cartilage Cells Using a Capacitively Coupled PEMF Signal

Introduction

A PEMF signal similar to that used clinically for bone repair is currently being tested for its ability to reduce pain in joints of arthritic patients. Of interest is whether this pain relief signal can also improve the underlying problem of impaired cartilage.

Background

Compared to drug therapies and biologics, PEMF based therapeutics offer a treatment that is easy to use, non-invasive, involves no foreign agent with potential side effects, and has zero clearance time. Issues with PEMF therapeutics include identifying responsive cells, elucidating a physical transduction site on a cell, and determining the biological mechanism of action that results in a cell response. The purpose of this study was to determine whether a specific PEMF signal currently being tested for pain relief (MEDRELIEF®, Healthonics, Inc, Ga.) could stimulate cartilage cells in vitro and whether a biological mechanism of action could be unraveled.

Methods

Normal human cartilage cells (HCC; CAMBREX®, Walkersville, Md.) were plated in rectangular cell chambers in monolayer. PEMF application was capacitively coupled through a niobium electrode bridge system which allowed a time varying current to flow uniformly through the chambers. A pulse-burst B-type signal as described herein is composed of a 10-msec burst of asymmetric rectangular pulses, 200/28 microseconds in width, repeated at 15 Hz. The PEMF signal was applied for 30 minutes per treatment. Cell growth was assessed by DNA content of the cell layer. Nitric oxide (NO) content of culture media was assessed by the Griess reaction using an assay kit from INVITROGEN INC.® (Carlsbad, Calif.). Results are expressed as micromoles of NO per cell number as assessed by DNA content of the cell layer.

Results

Figure 7:
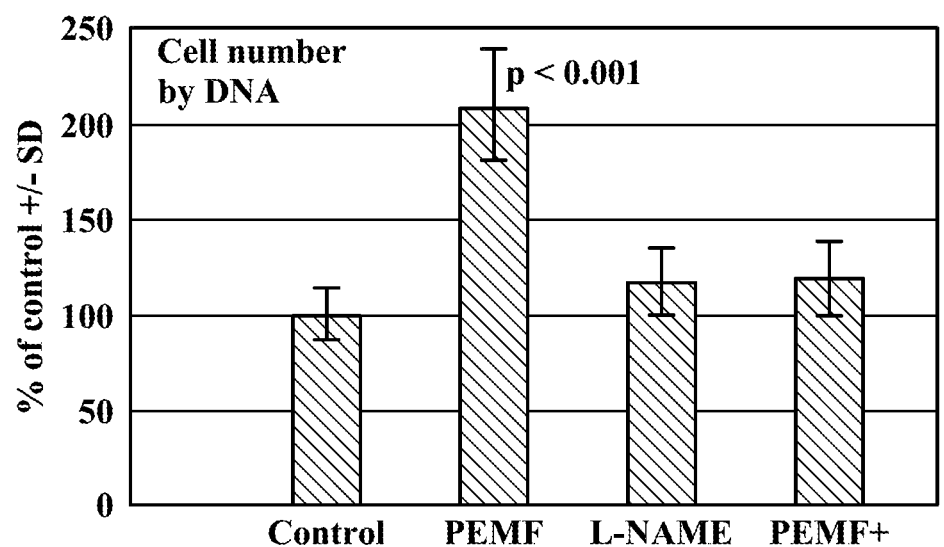
FIG. 7 provides a bar graph showing the increase in cell number measured by DNA as a percentage of control±standard deviation for PEMF signal waveforms in the presence and absence of L-NAME. L-NAME alone is presented as an experimental control.

A PEMF signal applied at 400 micro-amperes, peak-to-peak, to HCC cells grown in cultured media containing 1% fetal calf serum, every 12 hours over a 96 hour period resulted in increased cell growth of 153±22%, $p<0.001$. Of interest was conditioned culture media collected 24 hours after the first PEMF treatment shows and increase in NO of 196±14%, $p<0.001$ which declined to non-significant levels at 96 hours. Under similar conditions when SNP (an NO donor-sodium nitroprusside) was added to a final concentration of 3 micrograms/ml there was also an increase in NO at 24 hours (174±26%, $p<0.001$) and an increase in cell number at 96 hours (168±22%, $p<0.001$) compared to non-treated controls. In a subsequent experiment the serum concentration was reduced to 0.1%, the PEMF applied at 40 microAmps once every 24 hours, and measurements taken after 72 hours. PEMF treatment increased NO content in conditioned culture media to 154±30%, <0.01. As shown in FIG. 7, PEMF treatment increased cell number and this cell response was attenuated by L-NAME (a nitric oxide synthase inhibitor).

Conclusion

These results suggest that a PEMF signal currently being tested to reduce joint pain due to arthritis may also provide a benefit to cartilage. The data indicates human cartilage cells can respond to this signal with increased cell growth. Furthermore, a possible biologic mechanism of action for PEMF stimulated cartilage cell growth is through release of NO. A similar response of cartilage calls to an NO-donor supports this hypothesis. Although not conclusive, the data suggest that increased cell growth following PEMF treatment is either mediated by NO, or that NO is a required step in the mechanism for PEMF to produce increased cell growth.

Example 4

PEMF Stimulation of BMP Production in a Primary Osteoblast Culture: Dependence on Signal Configuration and Exposure Duration Introduction As an adjunct to surgery in spine fusion, or for treatment of recalcitrant non-unions in long bones, PEMF has proven effective as a non-surgical therapeutic. Pilot work has demonstrated that osteoblasts respond differently to both signal configuration and duration. One key difference included a proclivity for depositing matrix in lieu of cell proliferation. Based on a proven efficacy of BMP in spine fusion and in non-unions, and on efforts demonstrating that BMP-2 and BMP-4 are stimulated by PEMF (Bodamyali, 1998), our study focused on better understanding whether previous cell responses could be correlated with BMP regulation.

Objective

This study compared two PEMF waveform configurations delivered with capacitive coupling, correlating biochemical and morphologic variations in a primary bone cell culture with BMP regulation.

Methodology

Normal human osteoblast cells were established in 10 cm² individual culture chambers. Signals were applied to several chambers simultaneously by connecting them in series via niobium wires which acted as a coupling capacitance. Stimuli consisted of a continuous train of either 60/28 microseconds rectangular, bipolar pulses designated as "signal A", or 200/28 microsecond rectangular, bipolar pulses designated as signal B, applying peak to peak electric fields of 1.2 mV/cm (in A) or 2.4 mV/cm (in B) uniformly to the cultures. Cultures were exposed for 30 minutes (1), or 2 hours (2), twice a day, yielding groups A1, A2, B1 and B2 for comparison. Aliquots previously used for membrane protein determinations were analyzed for BMP protein by ELISA assay, and matrices previously used to determine calcium and interpret morphology were used to isolate RNA that was subsequently analyzed by a two-step reverse-transcriptase polymerase chain reaction (RT-PCR) using known and available sequence primers for (18s RNA) BMP-2 and BMP-7. Both the signal that stimulated proliferation and that which stimulated matrix deposition were analyzed for BMP regulation and protein translation. Samples from 7-, 14-, and 21-day time points were used to assure identical comparisons for the assay.

Results

The chief outcomes of this experiment were sixfold; 1) BMP protein and mRNA for BMP were elevated in response to both stimuli, particularly that of the "A" signal; 2) the 30 minute stimulus delivered twice per day offered nearly 40-fold increase in BMP-2 expression at 21 days compared to the 2-hour treatment, with the majority of the gain achieved during the period between 14-21 days; 3) the 30-minute stimulus for the "A" signal provided a 15-fold increase in BMP-7 expression, again almost entirely noted between the 14- and 21-day analyses; 4) only moderate increases in either BMP-2 or BMP-7 were seen with respect to the "B" signal; 5) this study provides the first evidence that BMP-7 expression is promoted by PEMF stimulation and 6) although the proliferation assessment was qualitative, the mitogenic nature of BMP deposition is in accord with previously published work. Work evaluating PEMF on a transformed cell line for short periods of time suggests that neither BMP-3 nor BMP-6 is stimulated (Yajima, 1996). We did not evaluate our model with respect to these growth factors.

Conclusion

Given the body of work that has shown BMP-2 to have morphogenetic and mitogenic properties, the proliferation of the cells in response to the "A" signal is not surprising. That the two signal configurations produced very different effects is potentially explainable by a SNR analysis that suggest the dose of signal "B" can be 10× higher than signal "A" with the assumption of a Ca/CaM transduction pathway. Perhaps more unexpected was the normalized BMP-2 and BMP-7 levels despite the exaggerated matrix deposition afforded by the "B" signal. Bone formation is acutely dependent on a balance of growth factor and microtopography of the surface—in fact, the presence of a smooth surface overrides the cell response to BMP-2 and accentuates dystrophic mineralization. Given the high degree of matrix organization and deposition seen in response to the "B" signal, BMP transduction in and of itself seems insufficient for productive bone formation and may occur by a separate targeting mechanism.

Example 5

Case Study: Treatment of Osteoporosis with PEMF Stimulation

One osteoporotic individual (female, age 50, T=−3.092 at start) used electrical stimulation using Signal B (200/30) for 4-5 days a week for 3-5 hours each day. The patient remained on the same medications, supplements and activity for a one year period. Follow up bone density scanning at 6 months and 12 months, revealed a 16% and 29% increase in bone mass density.

We claim:

1. A culture chamber to contain a fluid medium and a layer of cells, the culture chamber to include a top side, a bottom side, and one or more side walls, the culture chamber comprising:
   a bottom sheet arranged along the bottom side of the culture chamber, the bottom sheet to attach to the layer of cells, the layer of cells to be disposed parallel to and above the bottom sheet;
   a pair of electrodes arranged along the one or more side walls of the culture chamber, the pair of electrodes located on opposing sides of the culture chamber and arranged to be at least partially submerged by the fluid medium when the culture chamber is in operation;

and a load source, the load source to apply a stress to the layer of cells attached to the bottom sheet wherein the bottom sheet comprises a flexible membrane to flex in a direction towards the top side of the culture chamber, the flexible membrane to divide the culture chamber into an upper chamber comprised of a volume of the culture chamber above the flexible membrane and a lower chamber comprised of a volume of the culture chamber below the flexible membrane, and wherein the load source includes a pump that fluidly couples to the bottom side of the culture chamber at a location relatively below the bottom sheet, the pump to increase pressure in the lower chamber to flex the flexible membrane towards the top side of the culture chamber.

2. The culture chamber of claim 1 wherein at least one of the pair of electrodes is comprised of a self-protecting metal.

3. The culture chamber of claim 2 wherein the self-protecting metal includes one or more of niobium, tantalum, titanium, zirconium, molybdenum, tungsten, and vanadium.

4. The culture chamber of claim 1 wherein the flexible membrane is comprised of plasma-etched silicone rubber.

5. The culture chamber of claim 1 wherein the pump increases pressure in the lower chamber to flex the flexible membrane towards the top side of the culture chamber at a first time period and decreases pressure to the lower chamber to flex the flexible membrane towards the bottom side of the culture chamber at a second time period.

6. The culture chamber of claim 5 wherein the pump oscillate between an increase in pressure in the lower chamber to flex the flexible membrane towards the top side of the culture chamber and a decrease in pressure to the lower chamber to flex the flexible membrane towards the bottom side of the culture chamber.

7. The culture chamber of claim 1 wherein the load source includes a pump fluidly coupled to the culture chamber at a location above the bottom sheet, the pump to increase pressure in the culture chamber.

8. The culture chamber of claim 1 wherein the load source includes a piston located at the top side of the culture chamber, the piston to form a fluid-tight seal with the culture chamber and move in a direction towards the bottom side of the culture chamber.

9. The culture chamber of claim 1 wherein the load source includes a pump fluidly coupled to the culture chamber via a first port and a second port, the first port and the second port located opposite each other across the culture chamber and along the one or more side walls, the pump to create a flow of fluid medium within the culture chamber between the first port and the second port.

10. The culture chamber of claim 9 further comprising:
a first set of baffles located within the culture chamber proximate the first port, and
a second set of baffles located within the culture chamber proximate the second port,
wherein the first set of baffles and the second set of baffles are arranged to promote a uniform flow of the fluid medium between the first port and the second port.

11. The culture chamber of claim 1 wherein the bottom sheet includes a scaffold that includes growth-promoting and adhesion molecules.

* * * * *